(12) United States Patent
Marziali et al.

(10) Patent No.: US 9,434,938 B2
(45) Date of Patent: Sep. 6, 2016

(54) SYSTEMS AND METHODS FOR ENHANCED SCODA

(71) Applicant: The University of British Columbia, Vancouver (CA)

(72) Inventors: Andrea Marziali, North Vancouver (CA); Joel Pel, Vancouver (CA); Jason Donald Thompson, Vancouver (CA); Gosuke Shibahara, Vancouver (CA)

(73) Assignee: The University of British Columbia, Vancouver (CA)

( * ) Notice: Subject to any disclaimer, the term of this patent is extended or adjusted under 35 U.S.C. 154(b) by 505 days.

(21) Appl. No.: 13/968,907

(22) Filed: Aug. 16, 2013

(65) Prior Publication Data

US 2013/0323742 A1    Dec. 5, 2013

Related U.S. Application Data

(63) Continuation of application No. 13/153,185, filed on Jun. 3, 2011, now Pat. No. 8,518,228.

(60) Provisional application No. 61/488,585, filed on May 20, 2011.

(51) Int. Cl.
*C12N 15/10* (2006.01)
*G01N 33/53* (2006.01)
(Continued)

(52) U.S. Cl.
CPC ........... *C12N 15/1003* (2013.01); *B03C 7/023* (2013.01); *C12N 15/101* (2013.01); *C12Q 1/6806* (2013.01); *G01N 33/5308* (2013.01); *G01N 33/543* (2013.01);
(Continued)

(58) Field of Classification Search
CPC .................. C12N 2310/333–2310/336; C12N 2310/3521; G01N 27/447–27/44791
See application file for complete search history.

(56) References Cited

U.S. PATENT DOCUMENTS

| 4,148,703 A | 4/1979 | Trop et al. |
| 4,390,403 A | 6/1983 | Batchelder |

(Continued)

FOREIGN PATENT DOCUMENTS

| CA | 2552262 A1 | 8/2005 |
| CA | 2523089 A1 | 4/2006 |

(Continued)

OTHER PUBLICATIONS

V.L. Boyd, et al. "Methylation-dependent fragment separation: Direct detection of DNA methylation by capillary electrophoresis of PCR products from bisulfite-converted genomic DNA" Analytical Biochemistry, vol. 354, 2006, p. 266-273.*

(Continued)

*Primary Examiner* — J. Christopher Ball
(74) *Attorney, Agent, or Firm* — Brown Rudnick LLP; Thomas C. Meyers

(57) ABSTRACT

Methods and apparatus for separating, concentrating and/or detecting molecules based on differences in binding affinity to a probe are provided. The molecules may be differentially modified. The molecules may be differentially methylated nucleic acids. The methods can be used in fields such as epigenetics or oncology to selectively concentrate or detect the presence of specific biomolecules or differentially modified biomolecules, to provide diagnostics for disorders such as fetal genetic disorders, to detect biomarkers in cancer, organ failure, disease states, infection or the like.

18 Claims, 17 Drawing Sheets

(51) Int. Cl.

| | | |
|---|---|---|
| *G01N 33/543* | (2006.01) | |
| *G01N 33/574* | (2006.01) | |
| *G01N 33/68* | (2006.01) | |
| *C12Q 1/68* | (2006.01) | |
| *B03C 7/02* | (2006.01) | |

(52) U.S. Cl.
CPC ......... *G01N 33/574* (2013.01); *G01N 33/689* (2013.01); *G01N 2800/385* (2013.01)

(56) References Cited

U.S. PATENT DOCUMENTS

| | | |
|---|---|---|
| 4,390,404 A | 6/1983 | Esho et al. |
| 4,732,656 A | 3/1988 | Hurd |
| 4,830,726 A | 5/1989 | Stamato et al. |
| 4,911,817 A | 3/1990 | Kindlmann |
| 4,971,671 A | 11/1990 | Slater et al. |
| 5,084,157 A | 1/1992 | Clark et al. |
| 5,185,071 A | 2/1993 | Serwer et al. |
| 5,286,434 A | 2/1994 | Slater et al. |
| 5,302,510 A | 4/1994 | Klevan |
| 5,384,022 A | 1/1995 | Rajasekaran |
| 5,453,162 A | 9/1995 | Sabanayagam et al. |
| 5,609,743 A | 3/1997 | Sasagawa et al. |
| 5,641,628 A | 6/1997 | Bianchi |
| 5,938,904 A | 8/1999 | Bader et al. |
| 6,036,831 A | 3/2000 | Bishop |
| 6,110,670 A | 8/2000 | Van Broeckhoven et al. |
| 6,146,511 A | 11/2000 | Slater et al. |
| 6,193,866 B1 | 2/2001 | Bader et al. |
| 6,258,540 B1 | 7/2001 | Lo et al. |
| 6,693,620 B1 | 2/2004 | Herb et al. |
| 6,824,664 B1 | 11/2004 | Austin et al. |
| 6,827,830 B1 | 12/2004 | Slater et al. |
| 6,881,317 B2 | 4/2005 | Huang et al. |
| 6,893,546 B2 | 5/2005 | Jullien et al. |
| 6,927,028 B2 | 8/2005 | Dennis et al. |
| 7,175,747 B2 | 2/2007 | Bayerl et al. |
| 7,198,702 B1 | 4/2007 | Washizu et al. |
| 7,371,533 B2 | 5/2008 | Slater et al. |
| 7,427,343 B2 | 9/2008 | Han et al. |
| 7,442,506 B2 | 10/2008 | Dhallan |
| 7,452,668 B2 | 11/2008 | Boles et al. |
| 7,838,647 B2 | 11/2010 | Hahn et al. |
| 7,888,017 B2 | 2/2011 | Quake et al. |
| 8,008,018 B2 | 8/2011 | Quake et al. |
| 8,133,371 B2 | 3/2012 | Marziali et al. |
| 8,182,666 B2 | 5/2012 | Marziali et al. |
| 8,195,415 B2 | 6/2012 | Fan et al. |
| 2001/0045359 A1 | 11/2001 | Cheng et al. |
| 2002/0036139 A1 | 3/2002 | Becker et al. |
| 2002/0081280 A1 | 6/2002 | Curiel et al. |
| 2002/0119448 A1 | 8/2002 | Sorge et al. |
| 2002/0179445 A1 | 12/2002 | Alajoki et al. |
| 2003/0027178 A1 | 2/2003 | Vasmatzis et al. |
| 2003/0215855 A1 | 11/2003 | Dubrow et al. |
| 2005/0164241 A1 | 7/2005 | Hahn et al. |
| 2005/0164402 A1 | 7/2005 | Belisle et al. |
| 2005/0247563 A1 | 11/2005 | Shuber et al. |
| 2005/0247564 A1 | 11/2005 | Volkel et al. |
| 2007/0215472 A1 | 9/2007 | Slater et al. |
| 2007/0218494 A1 | 9/2007 | Slater et al. |
| 2008/0108063 A1 | 5/2008 | Lucero et al. |
| 2008/0314751 A1 | 12/2008 | Bukshpan et al. |
| 2009/0120795 A1 | 5/2009 | Marziali et al. |
| 2009/0139867 A1 | 6/2009 | Marziali et al. |
| 2009/0152116 A1 | 6/2009 | Boles et al. |
| 2010/0285537 A1 | 11/2010 | Zimmermann |
| 2011/0048950 A1 | 3/2011 | Marziali et al. |
| 2011/0245482 A1 | 10/2011 | Hahn et al. |
| 2011/0272282 A1 | 11/2011 | Marziali et al. |
| 2012/0048735 A1 | 3/2012 | Marziali et al. |
| 2012/0160682 A1 | 6/2012 | Marziali et al. |
| 2012/0199481 A1 | 8/2012 | Marziali et al. |

FOREIGN PATENT DOCUMENTS

| | | |
|---|---|---|
| CA | 2496294 A1 | 8/2006 |
| CA | 2641326 A1 | 8/2006 |
| CA | 2713313 A1 | 8/2009 |
| CA | 2742460 A1 | 5/2010 |
| EP | 0356187 A2 | 2/1990 |
| EP | 1720636 A1 | 11/2006 |
| EP | 1859249 A0 | 11/2007 |
| EP | 2238434 A0 | 10/2010 |
| EP | 2458004 A1 | 5/2012 |
| GB | 2249395 A | 5/1992 |
| JP | 7-167837 A | 7/1995 |
| JP | 2000-505545 A | 5/2000 |
| JP | 2001-165906 A | 6/2001 |
| JP | 2002-502020 A | 1/2002 |
| JP | 2003-062401 A | 3/2003 |
| JP | 2003-066004 A | 3/2003 |
| JP | 2003-513240 A | 4/2003 |
| JP | 2003-215099 A | 7/2003 |
| JP | 2003-247980 A | 9/2003 |
| WO | 9514923 A1 | 6/1995 |
| WO | 9727933 A1 | 8/1997 |
| WO | 9938874 A2 | 8/1999 |
| WO | 9945374 A2 | 9/1999 |
| WO | 0131325 A1 | 5/2001 |
| WO | 0242500 A2 | 5/2002 |
| WO | 03019172 A2 | 3/2003 |
| WO | 2005072854 A1 | 8/2005 |
| WO | 2006063625 A1 | 6/2006 |
| WO | 2006081691 A1 | 8/2006 |
| WO | 2007092473 A2 | 8/2007 |
| WO | 2009094772 A1 | 8/2009 |
| WO | 2010051649 A1 | 5/2010 |
| WO | 2010/104798 A1 | 9/2010 |
| WO | 2010121381 A1 | 10/2010 |
| WO | 2013002616 A2 | 1/2013 |

OTHER PUBLICATIONS

Asbury, et al., "Trapping of DNA by dielectrophoresis", Electrophoresis, 2002, 23:2658-2666.

Asbury, et al., "Trapping of DNA in Nonuniform Oscillating Electric Fields", Biophysical Journal, 1998, 74:1024-1030.

Astumian, et al., "Fluctuation Driven Ratchets: Molecular Motors", Physical Review Letters, 1994, 72(11):1766-1769.

Baba, Yoshinobu, " Capillary Affinity Gel Electrophoresis", Molecular Biotechnology, 1996, (9):1-11.

Bier, Martin, et al., "Biasing Brownian Motion in Different Directions in a 3-State Fluctuating Potential and an Application for the Separation of Small Particles", Physical Review Letters, 1996, 76(22):4277-4280.

Broemeling, D., et al., "An Instrument for Automated Purification of Nucleic Acids from Contaminated Forensic Samples", JALA 2008, 13, 40-48.

Carle, G.F., et al., "Electrophoretic Separations of Large DNA Molecules by Periodic Inversion of the Electric Field", Science, 1986, 232(4726):65-68.

Chacron, M.J., et al., "Particle trapping and self-focusing in temporarily asymmetric ratchets with strong field gradients", Physical Review E, 1997, 56(3):3446-3450.

Chakrabarti, Subrata, et al., "Highly Selective Isolation of Unknown Mutations in Diverse DNA Fragments: Toward New Multiplex Screening in Cancer", American Association for Cancer Reserch, 2000, 60:3732-3737.

Chan, K.C. Allen, et al., "Size Distributions of Maternal and Fetal DNA in Maternal Plasma," Molecular Diagnostics and Genetics, Clinical Chemistry, 2004, 50(1):88-92.

Chu, Gilbert, "Bag model for DNA migration during pulsed-field electrophoresis", Proc. Natl. Acad. Sci., 1991, 88:11071-11075.

European Search Report corresponding to EP11004417, Mar. 29, 2012, 4 pages.

Frumin, L.L., et al., "Anomalous size dependence of the non-linear mobility of DNA", In PhysChemComm, 2000, 11 (3):61-63.

Frumin, L.L., et al., "Nonlinear focusing of DNA macromolecules", Physical Review E—Statistical, Nonlinear and Soft Matter Physics, 2001, 64:021902-1-5.

(56) References Cited

OTHER PUBLICATIONS

Griess, Gary A., et al., "Cyclic capillary electrophoresis", Electrophoresis, 2002, 23:2610-2617.
International Preliminary Report on Patentability corresponding to PCT/CA2005/000124, Aug. 7, 2006, 8 pages.
International Preliminary Report on Patentability corresponding to PCT/CA2009/000111, Aug. 3, 2010, 9 pages.
International Search Report and Written Opinion for PCT/US13/39553, Sep. 18, 2013, 13 pages.
International Search Report dated Feb. 23, 2010 corresponding to PCT/CA2009/001648, 6 pages.
International Search Report for PCT/CA2006/000172, International Searching Authority, Jun. 2, 2006, 4 pages.
International Search Report for PCT/CA2012/050576, Feb. 28, 2013, 3 pages.
Jorgez, Carolina J., et al., "Quantity versus quality: Optimal methods for cell-free DNA isolation from plasma of pregnant women", American College of Medical Genetics, 2006, 8(10):615-619.
Kitzman, Jacob O., et al., "Noninvasive Whole-Genome Sequencing of a Human Fetus", Sci Transl Med 4, 137ra76 (2012); DOI: 10.1126/scitranslmed.3004323, 9 pages.
Kopecka, K, et al., "Capillary electrophoresis sequencing of small ssDNA molecules versus the Ogston regime: Fitting data and interpreting parameters", Electrophoresis, 2004, 25(14):2177-2185.
LaLande, Marc, et al., "Pulsed-field electrophoresis: Application of a computer model to the separation of large DNA molecules," Proc. Natl. Acad. Sci. USA, 1987, 84:8011-8015.
Lun, Fiona M. F., et al., "Microfluidics Digital PCR Reveals a Higher than Expected Fraction of Fetal DNA in Maternal Plasma," Molecular Diagnostics and Genetics, Clinical Chemistry, 2008, 54(10):1664-1672.
Magnasco, Marcelo, O., "Forced Thermal Ratchets", Physical Review Letters, 1993, 71(10):1477-1481.
Makridakis, Nick M., "PCR-free method detects high frequency of genomic instability in prostate cancer", Nucleic Acids Research, 2009, 37(22):7441-7446.
Marziali, A., et al., "Novel electrophoresis mechanism based on synchronous alternating drag perturbation", Electrophoresis 2005, 26:82-90, published on-line Dec. 29, 2004 at URL www.3.interscience.wiley.com/cgi-bin/issue/109861245.
Nollau, Peter, et al., "Methods for detection of point mutations: performance and quality assessment", Department of Clinical Chemistry, 1997, 43(7):1114-1128.
Office Action mailed Aug. 19, 2011 for U.S. Appl. No. 11/815,760.
Office Action mailed Dec. 27, 2010 for U.S. Appl. No. 11/815,760.
Pel, J., "A novel electrophoretic mechanism and separation parameter for selective nucleic acid concentration based on synchronous coefficient of drag alteration (SCODA)", (Ph.D. Thesis), Vancouver: University of British Columbia, 2009.
Pel, J., et al., "Nonlinear electrophoretic response yields a unique parameter for separation of biomolecules", PNAS 2009, vol. 106, No. 35, 14796-14801.
Rousseau, J., et al., "Gel electrophoretic mobility of single-stranded DNA: The two reptation field-dependent factors", Electrophoresis, 2000, 21(8)1464-1470.
Sikora, Aleksandra, et al., "Detection of Increased Amounts of Cell-Free DNA with Short PCR Amplicons," Clinical Chemistry, 2010, 56(1):136-138.
Slater, G.W., et al., "Recent developments in DNA electrophoretic separations", Electrophoresis, 1998, 19 (10):1525-1541.
Slater, G.W., et al., "Theory of DNA electrophoresis: A look at some current challenges", Electrophoresis, 2000, 21:3873-3887.
So. A., et al., "Efficient genomic DNA extraction from low target concentration bacterial cultures using SCODA DNA extraction technology", Cold Spring Harb Protoc, 2010, 1150-1153; 1185-1198.
Supplementary European Search Report corresponding to EP09706657, May 12, 2011, 2 pages.
Supplementary Partial European Search Report corresponding to EP05706448, May 14, 2012, 3 pages.
Tessier, F. et al., "Strategies for the separation of polyelectrolytes based on non-linear dynamics and entropic ratchets mple microfluidic device", Applied Physics A—Materials Science & Processing, 2002, 75:285-291.
Turmel, C., et al., "Molecular detrapping and band narrowing with high frequency modulation of pulsed field electrophoresis", Nucleic Acids Research, 1990, 18(3):569-575.
Viovy, J.L., "Electrophoresis of DNA and other polyelectrolytes: Physical mechanisms", Review of Modern Physics, 2000, 72(3):813-872.
Wright, Caroline, "Cell-free fetal nucleic acids for non-invasive prenatal diagnosis," Report of the UK export working group, Jan. 2009, 64 pages.
Yobas, L., et al., "Nucleic Acid Extraction, Amplification, and Detection on Si-Based Microfluidic Platforms," IEEE Journal of Solid-State Circuits, vol. 42, No. 8, Aug. 2007, 12 pages.

* cited by examiner

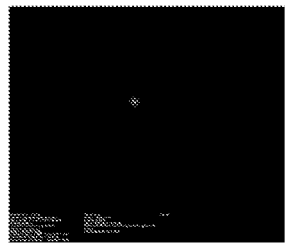 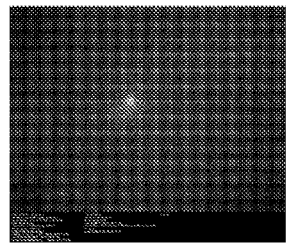 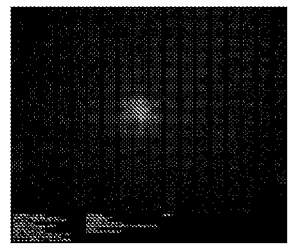
FIGURE 13A   FIGURE 13B   FIGURE 13C
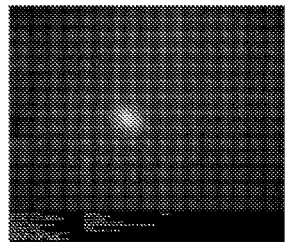
FIGURE 13D

SYSTEMS AND METHODS FOR ENHANCED SCODA

REFERENCE TO RELATED APPLICATION

This application is a continuation of U.S. application Ser. No. 13/153,185, filed Jun. 3, 2011, which claims the benefit of U.S. application Ser. No. 61/488,585, filed on 20 May 2011, entitled SYSTEMS AND METHODS FOR ENHANCED SCODA, the entirety of both of which are hereby incorporated by reference.

FIELD OF THE INVENTION

Embodiments of the present invention relate to the induced movement of particles such as nucleic acids, proteins and other molecules through media such as gels and other matrices. Some embodiments provide methods and apparatus for selectively purifying, separating, concentrating and/or detecting particles of interest. Some embodiments provide methods and apparatus for selectively purifying, separating, concentrating and/or detecting differentially modified particles of interest. Some embodiments provide methods and apparatus for selectively purifying, separating, concentrating and/or detecting differentially methylated DNA. Some embodiments are used in fields such as epigenetics, oncology, or various fields of medicine. Some embodiments are used to detect fetal genetic disorders, biomarkers indicative of cancer or a risk of cancer, organ failure, disease states, infections, or the like.

BACKGROUND

One mechanism for purifying, separating, or concentrating molecules of interest is called Synchronous Coefficient Of Drag Alteration (or "SCODA") based purification. SCODA, known in some embodiments as scodaphoresis, is an approach that may be applied for purifying, separating, or concentrating particles. SCODA may be applied, for example, to DNA, RNA and other molecules including proteins and polypeptides.

SCODA based transport is used to produce net motion of a molecule of interest by synchronizing a time-varying driving force, which would otherwise impart zero net motion, with a time-varying drag (or mobility) alteration. If application of the driving force and periodic mobility alteration are appropriately coordinated, the result is net motion despite zero time-averaged forcing. With careful choice of both the temporal and spatial configuration of the driving and mobility altering fields, unique velocity fields can be generated, in particular a velocity field that has a non-zero divergence, such that this method of transport can be used for separation, purification and/or concentration of particles.

SCODA is described in the following publications:
  U.S. Patent Publication No. 2009/0139867 entitled "Scodaphoresis and methods and apparatus for moving and concentrating particles";
  PCT Publication No. WO 2006/081691 entitled "Apparatus and methods for concentrating and separating particles such as molecules";
  PCT Publication No. WO 2009/094772 entitled "Methods and apparatus for particle introduction and recovery";
  PCT Publication No. WO 2009/001648 entitled "Systems and methods for enhanced SCODA"
  PCT Publication No. WO 2010/051649 entitled "Systems and methods for enhanced SCODA";
  PCT Publication No. WO 2010/121381 entitled "System and methods for detection of particles";
  Marziali, A.; Pel, J.; Bizotto, D.; Whitehead, L. A., "Novel electrophoresis mechanism based on synchronous alternating drag perturbation", Electrophoresis 2005, 26, 82-89;
  Broemeling, D.; Pel, J.; Gunn, D.; Mai, L.; Thompson, J.; Poon, H.; Marziali, A., "An Instrument for Automated Purification of Nucleic Acids from Contaminated Forensic Samples", JALA 2008, 13, 40-48;
  Pel, J.; Broemeling, D.; Mai, L.; Poon, H.; Tropini, G.; Warren, R.; Holt, R.; Marziali, A., "Nonlinear electrophoretic response yields a unique parameter for separation of biomolecules", PNAS 2008, vol. 106, no. 35, 14796-14801; and
  So, A.; Pel, J.; Rajan, S.; Marziali, A., "Efficient genomic DNA extraction from low target concentration bacterial cultures using SCODA DNA extraction technology", Cold Spring Harb Protoc 2010, 1150-1153,
each of which is incorporated herein by reference.

SCODA can involve providing a time-varying driving field component that applies forces to particles in some medium in combination with a time-varying mobility-altering field component that affects the mobility of the particles in the medium. The mobility-altering field component is correlated with the driving field component so as to provide a time-averaged net motion of the particles. SCODA may be applied to cause selected particles to move toward a focus area.

In one embodiment of SCODA based purification, described herein as electrophoretic SCODA, time varying electric fields both provide a periodic driving force and alter the drag (or equivalently the mobility) of molecules that have a mobility in the medium that depends on electric field strength, e.g. nucleic acid molecules. For example, DNA molecules have a mobility that depends on the magnitude of an applied electric field while migrating through a sieving matrix such as agarose or polyacrylamide[1]. By applying an appropriate periodic electric field pattern to a separation matrix (e.g. an agarose or polyacrylamide gel) a convergent velocity field can be generated for all molecules in the gel whose mobility depends on electric field. The field dependant mobility is a result of the interaction between a reptating DNA molecule and the sieving matrix, and is a general feature of charged molecules with high conformational entropy and high charge to mass ratios moving through sieving matrices. Since nucleic acids tend to be the only molecules present in most biological samples that have both a high conformational entropy and a high charge to mass ratio, electrophoretic SCODA based purification has been shown to be highly selective for nucleic acids.

The ability to detect specific biomolecules in a sample has wide application in the field of diagnosing and treating disease. Research continues to reveal a number of biomarkers that are associated with various disorders. Exemplary biomarkers include genetic mutations, the presence or absence of a specific protein, the elevated or reduced expression of a specific protein, elevated or reduced levels of a specific RNA, the presence of modified biomolecules, and the like. Biomarkers and methods for detecting biomarkers are potentially useful in the diagnosis, prognosis, and monitoring the treatment of various disorders, including cancer, disease, infection, organ failure and the like.

The differential modification of biomolecules in vivo is an important feature of many biological processes, including development and disease progression. One example of differential modification is DNA methylation. DNA methylation involves the addition of a methyl group to a nucleic acid. For example a methyl group may be added at the 5' position on the pyrimidine ring in cytosine[2]. Methylation of cytosine in CpG islands is commonly used in eukaryotes for long term regulation of gene expression[2]. Aberrant methylation patterns have been implicated in many human diseases including cancer. DNA can also be methylated at the 6 nitrogen of the adenine purine ring.

Chemical modification of molecules, for example by methylation, acetylation or other chemical alteration, may alter the binding affinity of a target molecule and an agent that binds the target molecule. For example, methylation of cytosine residues increases the binding energy of hybridization relative to unmethylated duplexes[3-5]. The effect is small. Previous studies report an increase in duplex melting temperature of around 0.7° C. per methylation site in a 16 nucleotide sequence[4] when comparing duplexes with both strands unmethylated to duplexes with both strands methylated.

There remains a need for methods and apparatus capable of providing improved separation and purification of molecules, including identical molecules that are differentially modified.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One embodiment provides a method for concentrating a molecule of interest from a biological sample. A biological sample is obtained from the subject and loaded on an affinity matrix. The affinity matrix has an immobilized affinity agent that has a first binding affinity for the molecule of interest and a second binding affinity for at least some of the other molecules in the biological sample. The first binding affinity is higher than the second binding affinity. Affinity SCODA is conducted to selectively concentrate the molecule of interest into a focus spot, wherein the concentration of the molecule of interest in the focus spot is increased relative to the concentration of the other molecules in the biological sample. The molecules may be nucleic acids. The molecule of interest may have the same sequence as at least some of the other molecules in the biological sample. The molecule of interest may be differentially modified as compared to at least some of the other molecules in the biological sample. The molecule of interest may be differentially methylated as compared to at least some of the other molecules in the biological sample. The biological sample may be maternal plasma and the molecule of interest may be fetal DNA that is differentially methylated as compared to maternal DNA. The biological sample may be a tissue sample and the molecule of interest may be a gene that is implicated in cancer that is differentially methylated as compared to the gene in a healthy subject.

One embodiment provides a method for separating a first molecule from a second molecule in a sample. An affinity matrix is provided with immobilized probes that bind to the first and second molecules. A binding energy between the first molecule and the probe is greater than a binding energy between the second molecule and the probe. A spatial gradient that is a mobility altering field that alters the affinity of the first and second molecules for the probe is provided within the affinity matrix. A driving field that effects motion of the molecules within the affinity matrix is applied. The orientation of both the spatial gradient and the driving field is varied over time to effect net motion of the first molecule towards a focus spot. A washing field is applied and is positioned to effect net motion of both the first and second molecules through the affinity matrix. The first and second molecules may be nucleic acids. The first and second molecules may be differentially modified. The first and second molecules may be differentially methylated. The first molecule may be fetal DNA and the second molecule may be maternal DNA that has the same sequence as the fetal DNA but is differentially methylated as compared to the fetal DNA. The first molecule and the second molecule may be a gene that is implicated in cancer, and the first molecule may be differentially methylated as compared to the second molecule.

One embodiment provides the use of a time-varying driving field in combination with a time-varying mobility altering field to separate first and second differentially methylated nucleic acid molecules, wherein the first and second nucleic acid molecules have the same DNA sequence. A time-varying driving field and a time-varying mobility altering field are applied to a matrix including an oligonucleotide probe that is at least partially complementary to said DNA sequence. The first nucleic acid molecule has a first binding energy to the oligonucleotide probe and the second nucleic acid molecule has a second binding energy to the oligonucleotide probe, and the first binding energy is higher than the second binding energy. The first nucleic acid molecules may be fetal DNA, the second nucleic acid molecules may be maternal DNA, and the first and second nucleic acid molecules may be obtained from a sample of maternal blood. The first and second nucleic acid molecules may be a gene that is implicated in a fetal disorder. The first and second molecules may be differentially methylated forms of a gene that is implicated in cancer. The first and second molecules may be obtained from a tissue sample of a subject.

One embodiment provides the use of synchronous coefficient of drag alteration (SCODA) to detect the presence of a biomarker in a subject.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. The embodiments and figures disclosed herein are to be considered illustrative rather than restrictive.

FIG. 10A shows the SCODA velocity field for perfect match target. A circular spot indicates final focus location. FIG. 10B shows the SCODA velocity field for the single base mismatch target.

FIGS. 13A, 13B, 13C and 13D show the results of performing SCODA focusing with different concentrations of probes and in the presence or absence of 200 mM NaCl. Probe concentrations are 100 µM, 10 µM, 1 µM, and 100 µM, respectively. The buffer used in FIGS. 13A, 13B and 13C was 1×TB with 0.2 M NaCl. The buffer used in FIG. 13D was 1×TBE. Different amounts of target were injected in each of these experiments, and the camera gain was adjusted prevent saturation.

FIGS. 21A and 21B show the results of an initial focus before washing unmethylated target from the gel for 10 pmol unmethylated DNA (FIG. 21A) and 0.1 pmol methylated DNA (FIG. 21B). FIGS. 21C and 21D show the results of a second focusing conducted after the unmethylated sequence had been washed from the gel for unmethylated and methylated target, respectively.

FIG. 22A shows the gel after loading. FIGS. 22B and 22C show focusing at 55° C. after 2 minutes and 4 minutes, respectively. FIGS. 22D and 22E show focusing at 62° C. after 2 minutes and 4 minutes, respectively. FIGS. 22 F, 22G and 22H show focusing of the target molecules to an extraction well at the centre of the gel after 0.5 minutes and 1 minute at 55° C. and at 3 minutes after raising the temperature to 62° C., respectively. FIGS. 22I, 22J and 22K show the application of a washing bias to the right at 55° C. after 6 minutes, 12 minutes and 18 minutes, respectively.

DETAILED DESCRIPTION

Figure 1:
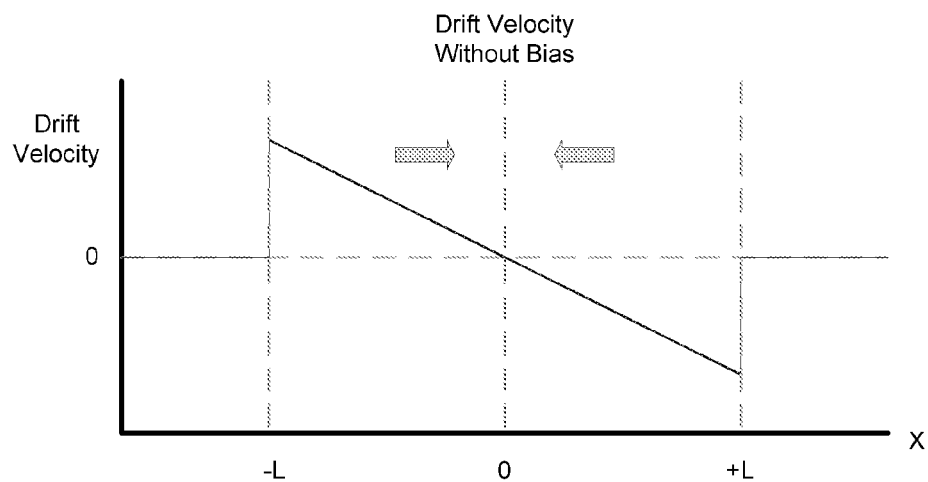
FIG. 1 shows a plot of equation [10] showing the SCODA drift velocity in one dimension over the domain extending from −L to +L.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

As used herein, the term "differentially modified" means two molecules of the same kind that have been chemically modified in different ways. Non-limiting examples of differentially modified molecules include: a protein or a nucleic acid that has been methylated is differentially modified as compared with the unmethylated molecule; a nucleic acid that is hypermethylated or hypomethylated (e.g. as may occur in cancerous or precancerous cells) is differentially modified as compared with the nucleic acid in a healthy cell; a histone that is acetylated is differentially modified as compared with the non-acetylated histone; and the like.

In some embodiments, molecules that are differentially modified are identical to one another except for the presence of a chemical modification on one of the molecules. In some embodiments, molecules that are differentially modified are very similar to one another, but not identical. For example, where the molecules are nucleic acids or proteins, one of the biomolecules may share at least 95%, at least 96%, at least 97%, at least 98%, or at least 99% sequence identity with the differentially modified molecule.

Affinity SCODA

SCODAphoresis is a previously documented method for injecting biomolecules into a gel, and preferentially concentrating nucleic acids or other biomolecules of interest in the center of the gel. SCODA may be applied, for example, to DNA, RNA and other molecules. Following concentration, the purified molecules may be removed for further analysis. In one specific embodiment of SCODAphoresis—affinity SCODA—binding sites which are specific to the biomolecules of interest may be immobilized in the gel. In doing so one may be able generate a non-linear motive response to an electric field for biomolecules that bind to the specific binding sites. One specific application of affinity SCODA is sequence-specific SCODA. Here oligonucleotides may be immobilized in the gel allowing for the concentration of only DNA molecules which are complementary to the bound oligonucleotides. All other DNA molecules which are not complementary may focus weakly or not at all and can therefore be washed off the gel by the application of a small DC bias.

SCODA based transport is a general technique for moving particles through a medium by first applying a time-varying forcing (i.e. driving) field to induce periodic motion of the particles and superimposing on this forcing field a time-varying perturbing field that periodically alters the drag (or equivalently the mobility) of the particles (i.e. a mobility-altering field). Application of the mobility-altering field is coordinated with application of the forcing field such that the particles will move further during one part of the forcing cycle than in other parts of the forcing cycle. Specifically, the drift velocity υ(t) of a particle driven by an external force F(t) with a time varying drag coefficient ζ(t) (i.e. a varying mobility) is given by:

$$v(t) = \frac{F(t)}{\zeta(t)} \quad [1]$$

If the external force and drag coefficient vary periodically such that $$F(t) = F_0 \sin(\omega t) \quad [2]$$

and, $$\frac{1}{\zeta(t)} = \frac{1}{\zeta_0} + \frac{\sin(\omega t + \phi)}{\zeta_1} \quad [3]$$

then the drift velocity averaged over one complete cycle is given by:

$$\overline{v}(t) = \frac{F_0}{2\zeta_1}\cos(\phi) \quad [4]$$

By varying the drag (i.e. mobility) of the particle at the same frequency as the external applied force, a net drift can be induced with zero time-averaged forcing. The result of equation [4] can be used with an appropriate choice of driving force and drag coefficients that vary in time and space to generate a convergent velocity field in one or two dimensions. A time varying drag coefficient and driving force can be utilized in a real system to specifically concentrate (i.e. preferentially focus) only certain molecules, even where the differences between the target molecule and one or more non-target molecules are very small, e.g. molecules that are differentially modified at one or more locations, or nucleic acids differing in sequence at one or more bases.

One Dimensional SCODA Concentration

By combining a spatially uniform driving force that varies periodically in time, with a drag coefficient that varies in time as well as in space it is possible to generate a convergent velocity field in one dimension. Consider the case of a charged particle with mobility μ moving under the influence of an applied electric field E; its velocity will be given by:

$$v(x,t)=\mu(x,t)E(x,t) \quad [5]$$

If electric field is varied periodically in time such that:

$$E(x,t)=E_0 \sin(\omega t) \quad [6]$$

and a linear mobility gradient is provided within the domain −L≤x≤L that varies at the same period:

$$\mu(x,t)=\mu_0+(kx)\sin(\omega t+\phi) \quad [7]$$

where k can be thought of as the amplitude of the mobility variation, SCODA-based separation of particles can be achieved.

There are a number of ways to establish a mobility gradient for charged molecules moving in solution under the influence of an applied external electric field. For example, a time-varying electric field may be provided as described above, a temperature gradient may be established, a pH gradient may be established, a light gradient may be established for molecules which undergo a conformational change in the presence or absence of light, or the like.

With the mobility gradient of equation [7] provided, the velocity becomes:

$$v(x,t)=[\mu_0+(kx)\sin(\omega t+\phi)][E_0 \sin(\omega t)] \quad [8]$$

Taking the time average of this velocity over one complete cycle yields the following drift velocity:

$$\overline{v}_d(x, t) = \frac{\omega}{2\pi}\int_0^{\frac{2\pi}{\omega}} v(x, t)\,dt \quad [9]$$

$$\overline{v}_d(x, t) = \frac{kx}{2}E_0 \cos(\phi) \quad [10]$$

This velocity field has an equilibrium point at x=0 and can be made convergent or divergent depending on the sign of $kE_0 \cos(\phi)$. For positive values the velocity field is divergent and for negative values it is convergent. FIG. 1 shows the velocity plotted as a function of x for the case where $kE_0 \cos(\phi)<0$. The arrows in FIG. 1 indicate the direction of drift. All particles between −L and +L will drift towards the zero velocity point at x=0. Outside of the domain the time averaged velocity is zero as the mobility is only altered between −L and +L.

In the embodiment illustrated in FIG. 1, the velocity takes on a positive value for negative values of x and vice versa for positive values of x resulting in all particles within the domain drifting towards x=0 where the velocity is zero.

Two Dimensional SCODA

To extend the result of equation [10] to two dimensions, in some embodiments a rotating electric field is used as the driving field and a rotating mobility gradient is established:

$$\vec{E} = E_0 \cos(\omega t)\hat{i} - E_0 \sin(\omega t)\hat{j} \quad [11]$$

$$\mu = \mu_0 + k[x \cos(\omega t + \phi) - y \sin(\omega t + \phi)] \quad [12]$$

As in the one dimensional case $\vec{\upsilon} = \mu \vec{E}$, and the same integration as in equation [9] can be performed to yield the time averaged drift velocity in two dimensions:

$$\overline{v}_x = \frac{\omega}{2\pi} \int_0^{\frac{2\pi}{\omega}} E_0 \cos(\omega t)(\mu_0 + k(x \cos(\omega t + \phi) - y \sin(\omega t + \phi))) dt \quad [13]$$

$$\overline{v}_y = \frac{\omega}{2\pi} \int_0^{\frac{2\pi}{\omega}} -E_0 \cos(\omega t)(\mu_0 + k(x \cos(\omega t + \phi) - y \sin(\omega t + \phi))) dt \quad [14]$$

This results in the following expression for the drift velocity:

$$\vec{v} = \frac{E_0 k}{2}((x \cos(\phi) - y \sin(\phi))\hat{i} + (x \sin(\phi) + y \cos(\phi))\hat{j}) \quad [15]$$

Rewriting in polar coordinates and simplifying yields:

$$\vec{v} = \frac{E_0 k r}{2}(\cos(\phi)\hat{r} + \sin(\phi)\hat{\theta}) \quad [16]$$

This result highlights a number of aspects of SCODA in two dimensions. It shows that despite the zero time averaged forcing there will be non-zero drift everywhere except at the point in the medium where r=0. It shows that the nature of the drift depends on the relative phase, ϕ, of the two signals, with the strength of focusing (the radial, r̂, term) being proportional to the cosine of the phase lag between the electric driving field oscillations and the mobility oscillations. For a 0° phase angle there is a purely focusing velocity field with net drift directed towards the centre of the domain. For a 180° phase angle the velocity field is pure de-focusing with net drift away from the centre of the gel. And for phase angles of 90° and 270° the velocity field is purely rotational. At intermediate angles the resultant velocity field will be a combination of both rotational and focusing components. To achieve efficient focusing, in some embodiments the phase difference between the driving force and the mobility variation is as small as possible.

Generation of a Time Varying Mobility Field

Previous applications of SCODA based concentration used the fact that the mobility of DNA in a sieving matrix such as agarose or polyacrylamide depends on the magnitude of the applied electric field. In some applications, the molecules of interest may have a mobility that does not normally depend strongly on electric field, such as short nucleic acids less than 200 bases, biomolecules other than nucleic acids (e.g. proteins or polypeptides), or the like. In some applications, it may be desired to purify only a subset of the nucleic acids in a sample, for example purifying or detecting a single gene from a sample of genomic DNA or purifying or detecting a chemically modified molecule (e.g. methylated DNA) from a differentially modified molecule having the same basic structure (e.g. unmethylated DNA having the same sequence), or the like.

SCODA-based purification of molecules that do not have a mobility that is strongly dependent on electrical field strength (i.e. which have a low value of k based on variations in electric field strength) can be achieved by using a SCODA matrix that has an affinity to the molecule to be concentrated. An affinity matrix can be generated by immobilizing an agent with a binding affinity to the target molecule (i.e. a probe) in a medium. Using such a matrix, operating conditions can be selected where the target molecules transiently bind to the affinity matrix with the effect of reducing the overall mobility of the target molecule as it migrates through the affinity matrix. The strength of these transient interactions is varied over time, which has the effect of altering the mobility of the target molecule of interest. SCODA drift can therefore be generated. This technique is called affinity SCODA, and is generally applicable to any target molecule that has an affinity to a matrix.

Affinity SCODA can selectively enrich for nucleic acids based on sequence content, with single nucleotide resolution. In addition, affinity SCODA can lead to different values of k for molecules with identical DNA sequences but subtly different chemical modifications such as methylation. Affinity SCODA can therefore be used to enrich for (i.e. preferentially focus) molecules that differ subtly in binding energy to a given probe, and specifically can be used to enrich for methylated, unmethylated, hypermethylated, or hypomethylated sequences.

Exemplary media that can be used to carry out affinity SCODA include any medium through which the molecules of interest can move, and in which an affinity agent can be immobilized to provide an affinity matrix. In some embodiments, polymeric gels including polyacrylamide gels, agarose gels, and the like are used. In some embodiments, microfabricated/microfluidic matrices are used.

Exemplary operating conditions that can be varied to provide a mobility altering field include temperature, pH, salinity, concentration of denaturants, concentration of catalysts, application of an electric field to physically pull duplexes apart, or the like.

Exemplary affinity agents that can be immobilized on the matrix to provide an affinity matrix include nucleic acids having a sequence complementary to a nucleic acid sequence of interest, proteins having different binding affinities for differentially modified molecules, antibodies specific for modified or unmodified molecules, nucleic acid aptamers specific for modified or unmodified molecules, other molecules or chemical agents that preferentially bind to modified or unmodified molecules, or the like.

The affinity agent may be immobilized within the medium in any suitable manner. For example where the affinity agent is an oligonucleotide, the oligonucleotide may be covalently bound to the medium, acrydite modified oligonucleotides may be incorporated directly into a polyacrylamide gel, the oligonucleotide may be covalently bound to a bead or other construct that is physically entrained within the medium, or the like.

Where the affinity agent is a protein or antibody, in some embodiments the protein may be physically entrained within the medium (e.g. the protein may be cast directly into an agarose or polyacrylamide gel), covalently coupled to the medium (e.g. through use of cyanogen bromide to couple the protein to an agarose gel), covalently coupled to a bead that is entrained within the medium, bound to a second affinity agent that is directly coupled to the medium or to beads entrained within the medium (e.g. a hexahistidine tag bound to NTA-agarose), or the like.

Where the affinity agent is a protein, the conditions under which the affinity matrix is prepared and the conditions under which the sample is loaded should be controlled so as not to denature the protein (e.g. the temperature should be maintained below a level that would be likely to denature the protein, and the concentration of any denaturing agents in the sample or in the buffer used to prepare the medium or conduct SCODA focusing should be maintained below a level that would be likely to denature the protein).

Where the affinity agent is a small molecule that interacts with the molecule of interest, the affinity agent may be covalently coupled to the medium in any suitable manner.

One exemplary embodiment of affinity SCODA is sequence-specific SCODA. In sequence specific SCODA, the target molecule is or comprises a nucleic acid molecule having a specific sequence, and the affinity matrix contains immobilized oligonucleotide probes that are complementary to the target nucleic acid molecule. In some embodiments, sequence specific SCODA is used both to separate a specific nucleic acid sequence from a sample, and to separate and/or detect whether that specific nucleic acid sequence is differentially modified within the sample. In some such embodiments, affinity SCODA is conducted under conditions such that both the nucleic acid sequence and the differentially modified nucleic acid sequence are concentrated by the application of SCODA fields. Contaminating molecules, including nucleic acids having undesired sequences, can be washed out of the affinity matrix during SCODA focusing. A washing bias can then be applied in conjunction with SCODA focusing fields to separate the differentially modified nucleic acid molecules as described below by preferentially focusing the molecule with a higher binding energy to the immobilized oligonucleotide probe.

Mobility of a Target in an Affinity Matrix

The interactions between a target and immobilized probes in an affinity matrix can be described by first order reaction kinetics:

$$[T] + [P] \underset{k_r}{\overset{k_f}{\rightleftharpoons}} [T \ldots P] \quad [17]$$

Here [T] is the target, [P] the immobilized probe, [T. P] the probe-target duplex, $k_f$ is the forward (hybridization) reaction rate, and $k_r$ the reverse (dissociation) reaction rate. Since the mobility of the target is zero while it is bound to the matrix, the effective mobility of the target will be reduced by the relative amount of target that is immobilized on the matrix:

$$\mu_{effective} = \mu_0 \frac{[T]}{[T] + [T \ldots P]} \quad [18]$$

where $\mu_0$ is the mobility of the unbound target. Using reasonable estimates for the forward reaction rate[6] and an immobilized probe concentration that is significantly higher than the concentration of the unbound target, it can be assumed that the time constant for hybridization should be significantly less than one second. If the period of the mobility-altering field is maintained at longer than one second, it can be assumed for the purposes of analysis that the binding kinetics are fast and equation [17] can be rewritten in terms of reaction rates:

$$k_f[T][P] = k_r[T \ldots P] \quad [19]$$

$$[T] = \frac{k_r}{k_f} \frac{[T \ldots P]}{[P]} \quad [20]$$

Inserting [20] into equation [18] and simplifying yields:

$$\mu_{effective} = \mu_0 \frac{1}{1 + \frac{k_f}{k_r}[P]} \quad [21]$$

From this result it can be seen that the mobility can be altered by modifying either the forward or reverse reaction rates. Modification of the forward or reverse reaction rates can be achieved in a number of different ways, for example by adjusting the temperature, salinity, pH, concentration of denaturants, concentration of catalysts, by physically pulling duplexes apart with an external electric field, or the like. In one exemplary embodiment described in greater detail below, the mechanism for modifying the mobility of target molecules moving through an affinity matrix is control of the matrix temperature.

To facilitate analysis, it is helpful to make some simplifying assumptions. First it is assumed that there are a large number of immobilized probes relative to target molecules. So long as this is true, then even if a large fraction of the target molecules become bound to the probes the concentration of free probes, [P], will not change much and it can be assumed that [P] is constant. Also, it is assumed that the forward reaction rate $k_f$ does not depend on temperature. This not strictly true, as the forward reaction rate does depend on temperature[7,8]. Secondary structure in the immobilized probe or in the target molecule can result in a temperature dependant forward reaction rate[9]. However, in embodiments operating at a temperature range near the duplex melting temperature the reverse reaction rate has an exponential dependence on temperature and the forward reaction rate has a much weaker temperature dependence, varying by about 30% over a range of 30° C. around the melting temperature[10]. It is additionally assumed that the target sequence is free of any significant secondary structure. Although this final assumption would not always be correct, it simplifies this initial analysis.

To determine the temperature dependence of the reverse reaction rate, an Arrhenius model for unbinding kinetics is assumed. This assumption is justified by recent work in nanopore force spectroscopy[11,12].

$$k_r = Ae^{\frac{\Delta G}{k_b T}} \quad [22]$$

Here A is an empirically derived constant, $\Delta G$ is the probe-target binding energy, $k_b$ is the Boltzmann constant, and T the temperature. Inserting this into [21], rewriting the free energy $\Delta G$ as $\Delta H - T\Delta S$, and collecting constant terms allows the mobility to be rewritten as:

$$\mu_{\mathit{effective}} = \mu_0 \frac{1}{1 + \beta e^{\frac{-\Delta H + T\Delta S}{k_b T}}} \quad [23]$$

Figure 2:
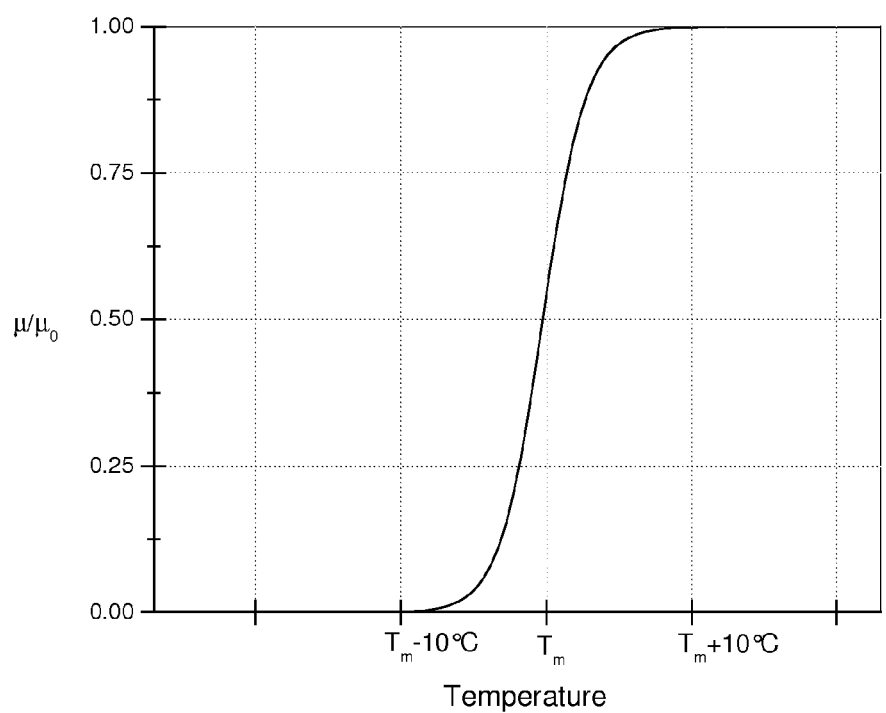
FIG. 2 shows a plot of equation [23] near the duplex melting temperature $T_m$ illustrating the relative change in mobility as a function of temperature.

Equation [23] describes a sigmoidal mobility temperature dependence. The shape of this curve is shown in FIG. 2. At low temperature the mobility is nearly zero. This is the regime where thermal excitations are insufficient to drive target molecules off of the affinity matrix. At high temperature target molecules move at the unbound mobility, where the thermal energy is greater than the binding energy. Between these two extremes there exists a temperature range within which a small change in temperature results in a large change in mobility. This is the operating regime for embodiments of affinity SCODA that utilize temperature as the mobility altering parameter.

In embodiments of affinity SCODA used to separate nucleic acids based on sequence, i.e. sequence-specific SCODA, this temperature range tends to lie near the melting temperature of the probe-target duplex. Equations [10] and [16] state that the speed of concentration is proportional to k, which is a measure of how much the mobility changes during one SCODA cycle. Operating near the probe-target duplex melting temperature, where the slope of the mobility versus temperature curve is steepest, maximizes k for a given temperature swing during a SCODA cycle in embodiments where temperature is used as the mobility altering parameter.

In some embodiments, affinity SCODA may be conducted within a temperature gradient that has a maximum amplitude during application of SCODA focusing fields that varies within about ±20° C., within about ±10° C., within about ±5° C., or within about ±2° C. of the melting temperature of the target molecule and the affinity agent.

It is possible to describe affinity SCODA in one dimension by replacing the time dependent mobility of equation [7] with the temperature dependent mobility of equation [23] and a time dependent temperature:

$$T(x, t) = T_m + T_a \left(\frac{x}{L}\right) \sin(\omega t + \phi) \quad [24]$$

Here, the temperature oscillates around $T_m$, the probe target melting temperature, and $T_a$ is the maximum amplitude of the temperature oscillations at $x = \pm L$. To get an analytical expression for the drift velocity, $\upsilon_d = \mu E$, as a function of temperature, a Taylor expansion of equation [23] is performed around $T_m$:

$$\mu_{\mathit{effective}} = \mu(T_m) - \frac{\mu_0 \beta \Delta H e^{\frac{-\Delta H + T\Delta S}{k_b T_m}}}{k_b T_m^2 \left(1 + \beta e^{\frac{-\Delta H + T\Delta S}{k_b T_m}}\right)^2} (T - T_m) + O((T - T_m)^2) \quad [25]$$

which can be rewritten as:

$$\mu\mathit{effective} = \mu(T_m) + \alpha(T - T_m) + O((T - T_m)^2) \quad [26]$$

Here the first term in the Taylor expansion has been collected into the constant $\alpha$. Combining [24] and [26] into an expression for the mobility yields an expression similar to [7]:

$$\mu(t) = \mu(T_m) + \left(\frac{\alpha T_a x}{L}\right) \sin(\omega t + \phi) \quad [27]$$

Equation [27] can be used to determine the time averaged drift velocity for both the one dimensional and two dimensional cases by simply replacing k with:

$$\alpha \frac{T_a}{L} = \frac{\mu_0 \beta \Delta H e^{\frac{-\Delta H + T\Delta S}{k_b T_m}}}{k_b T_m^2 \left(1 + \beta e^{\frac{-\Delta H + T\Delta S}{k_b T_m}}\right)^2} \left(\frac{T_a}{L}\right) \quad [28]$$

The drift velocity is then given by:

$$\overline{v}_d(x, t) = \frac{\alpha T_a x}{2L} E_0 \cos(\phi) \quad [29]$$

in one dimension, and:

$$\vec{v} = \frac{E_0 \alpha T_a r}{2L} (\cos(\phi) \hat{r} + \sin(\phi) \hat{\theta}) \quad [30]$$

in two dimensions. This result shows that if a two dimensional gel functionalized with immobilized probes (i.e. an affinity matrix), then by combining a rotating temperature gradient with a rotating dipole electric field, all target molecules should be forced towards a central region in the gel, thus concentrating a target molecule that binds to the immobilized probes.

Molecular Separation with Affinity SCODA

In some embodiments, affinity SCODA is used to separate two similar molecules (e.g. the same molecule that has been differentially modified, or which differs in sequence at only one or a few locations) with differing binding affinities for the immobilized probe. Beginning with two molecular species, each with a different binding energy to the immobilized probes, these two molecular species can be separated by superimposing a washing motive force over the driving and mobility altering fields used to produce SCODA focusing, to provide net motion of molecules that have a lesser binding affinity for the immobilized probe (i.e. the molecules that have a higher binding affinity for the immobilized probe are preferentially focused during the application of the SCODA focusing fields). In some embodiments, the washing force is a small applied DC force, referred to herein as a DC bias.

In the one dimensional case when a small DC force is applied as a washing or bias force, the electric field becomes:

$$E(x,t) = E_0 \sin(\omega t) + E_b \quad [31]$$

where $E_b$ is the applied DC bias. The final drift velocity has superimposed on the SCODA focusing velocity a constant velocity proportional to the strength of the bias field:

$$\overline{v}_d(x, t) = \frac{\alpha T_a x}{2L} E_0 \cos(\phi) + \mu(T_m) E_b \quad [32]$$

This drift velocity will tend to move the final focus location either to the left or right depending on the direction of bias. The amount by which this bias moves a focus off centre depends on the strength of the interaction between the target and probe molecules. The differential strength of the target-probe interaction can therefore serve as a mechanism to enable molecular separation of two highly similar species.

Figure 3:
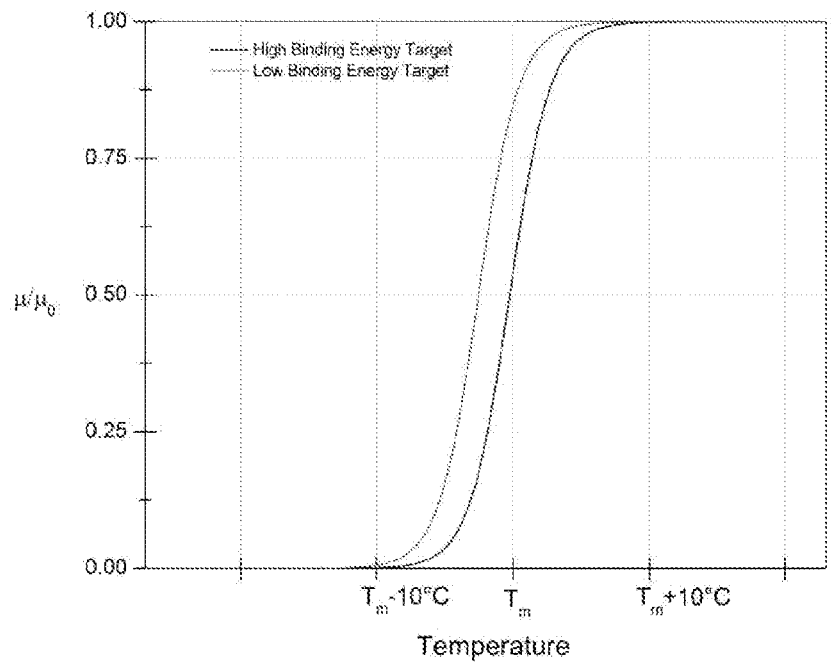
FIG. 3 shows a plot of mobility versus temperature for two different molecules with different binding energies to immobilized probe molecules. The mobility of the high binding energy target is shown by the curve on the right, while the mobility of the low binding energy target is shown by the curve on the left.

Consider two molecules that have different binding affinities for an immobilized probe. Reducing the probe-target binding energy, $\Delta G$ in equation [23], will serve to shift the mobility versus temperature curve to the left on the temperature scale as shown in FIG. 3. The mobility of the high binding energy target is shown by the curve on the right, while the mobility of the low binding energy target is shown by the curve on the left.

If the SCODA system in this exemplary embodiment is operated at the optimal focusing temperature for the higher binding energy molecule, $T_m$ in FIG. 3, then the mobility of the lower binding energy molecule will be higher and will have weaker temperature dependence. In terms of equation [32] the molecule with lower binding energy will have a larger value of $\mu(T_m)$ and a smaller value of a. This means that a lower binding energy molecule will have a lower SCODA drift velocity and a higher velocity under DC bias, resulting in a different final focus location than the high binding energy molecule as illustrated in FIG. 4.

Figure 4:
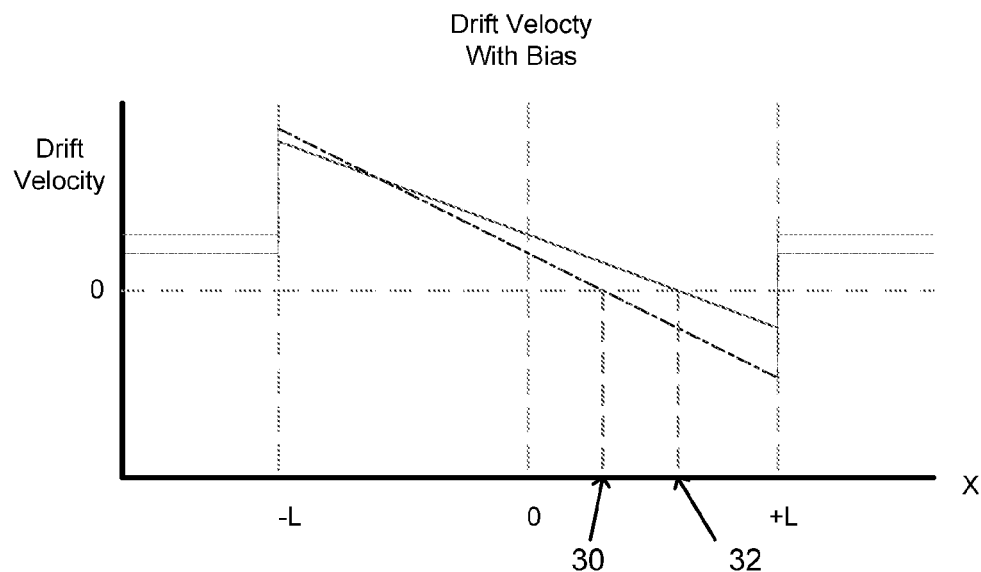
FIG. 4 shows the effect of an applied DC washing bias on molecules with two different binding energies. The solid curve represents the drift velocity of a target molecule with a lower binding energy to the bound probes than the molecules represented by the dashed curve.

FIG. 4 shows the effect of an applied DC bias on molecules with two different binding energies for the immobilized probe according to one embodiment. The solid curve represents the drift velocity of a target molecule with a lower binding energy to the bound probes than the molecules represented by the dashed curve. The final focus location is the point where the drift velocity is equal to zero. The molecules represented by the solid curve have both a lower SCODA drift velocity and a higher DC velocity compared to the molecules represented by the dashed curve. When SCODA focusing is combined with a DC bias the lower binding energy molecules will focus further away from the unbiased focus at x=0, resulting in two separate foci, one for each molecular species. The final focus position for the high binding energy molecule is indicated by reference numeral 30. The final focus position for the low binding energy molecule is indicated by reference numeral 32.

The two dimensional case is the same as the one dimensional case, the superimposed velocity from the applied washing bias moves the final focus spot off centre in the direction of the washing bias.

In some embodiments, if the difference in binding energies between the molecules to be separated is large enough and a sufficiently high washing bias is applied, the low binding energy molecules can be washed off of the affinity matrix while molecules with higher binding energy are retained in the affinity matrix, and may be captured at a focus location within the affinity matrix (i.e. preferentially focused) through the application of SCODA focusing fields.

Generation of a Time Varying Temperature Gradient

Embodiments of affinity SCODA that use variations in temperature as the mobility altering field may use a periodically varying temperature gradient to produce a convergent velocity field. A periodically varying temperature gradient may be provided in any suitable manner, for example by the use of heaters or thermoelectric chillers to periodically heat and cool regions of the medium, the use of radiative heating to periodically heat regions of the medium, the application of light or radiation to periodically heat regions of the medium, Joule heating using the application of an electric field to the medium, or the like.

A periodically varying temperature gradient can be established in any suitable manner so that particles that are spaced a farther distance from a desired focus spot experience greater mobility (i.e. are at a higher temperature and hence travel farther) during times of application of the driving field towards the desired focus spot than during times of application of the driving field away from the desired focus spot. In some embodiments, the temperature gradient is rotated to produce a convergent velocity field in conjunction with the application of a time-varying driving force.

In some embodiments, Joule heating using an electric field is used to provide a temperature gradient. In some embodiments, the electric field used to provide Joule heating to provide a temperature gradient is the same as the electric field that provides the driving field. In some embodiments, the magnitude of the electric field applied is selected to produce a desired temperature gradient within an affinity matrix.

In some embodiments, a spatial temperature gradient is generated using a quadrupole electric field to provide the Joule heating. In some such embodiments, a two dimensional gel with four electrodes is provided. Voltages are applied to the four electrodes such that the electric field in the gel is non-uniform, containing regions of high electric field (and consequently high temperature) and low electric field. The electric field is oriented such that the regions of high electric field tend to push negatively charged molecules towards the centre of the gel, while regions of low electric field tend to push such molecules away from the centre of the gel. In some such embodiments, the electric field that provides the temperature gradient through Joule heating is also the electric field that applies a driving force to molecules in the gel.

Figure 5:
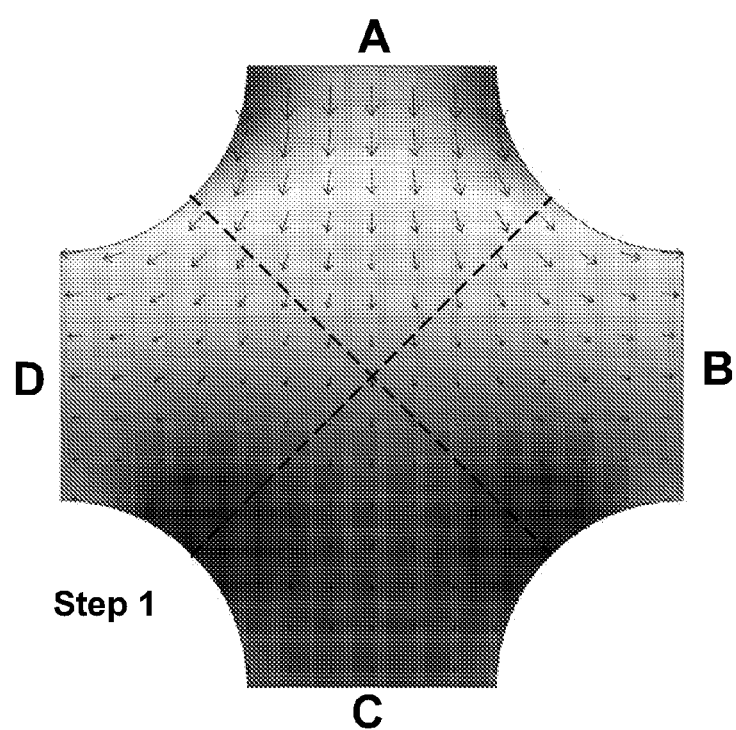
FIG. 5 shows an example of an electric field pattern suitable for two dimensional SCODA based concentration in some embodiments. Voltages applied at electrodes A, B, C and D, are −V, 0, 0, and 0 respectively. Arrows represent the velocity of a negatively charged analyte molecule such as DNA. Colour intensity represents electric field strength.

An example of such a field pattern is illustrated in FIG. 5. Voltages applied at electrodes A, B, C and D in FIG. 5 are −V, 0, 0, and 0 respectively. Arrows represent the velocity of a negatively charged analyte molecule. Colour intensity represents electric field strength. The regions near electrode A have a high electric field strength, which decreases towards electrode C. The high field regions near electrode A tend to push negatively charged molecules towards the centre of the gel, while the lower field regions near electrodes B, C, and D tend to push negatively charged molecules away from the centre of the gel. In embodiments in which the electric field also provides the temperature gradient, the affinity matrix will become hotter in regions of higher field strength due to Joule heating. Hence, regions of high electric field strength will coincide with regions of higher temperature and thus higher mobility. Accordingly, molecules in the high electric field regions near electrode A will tend to move a greater distance toward the centre of the gel, while molecules in the lower electric field regions near electrodes B, C, and D have a lower mobility (are at a cooler temperature) and will move only a short distance away from the centre of the gel.

Figure 6:
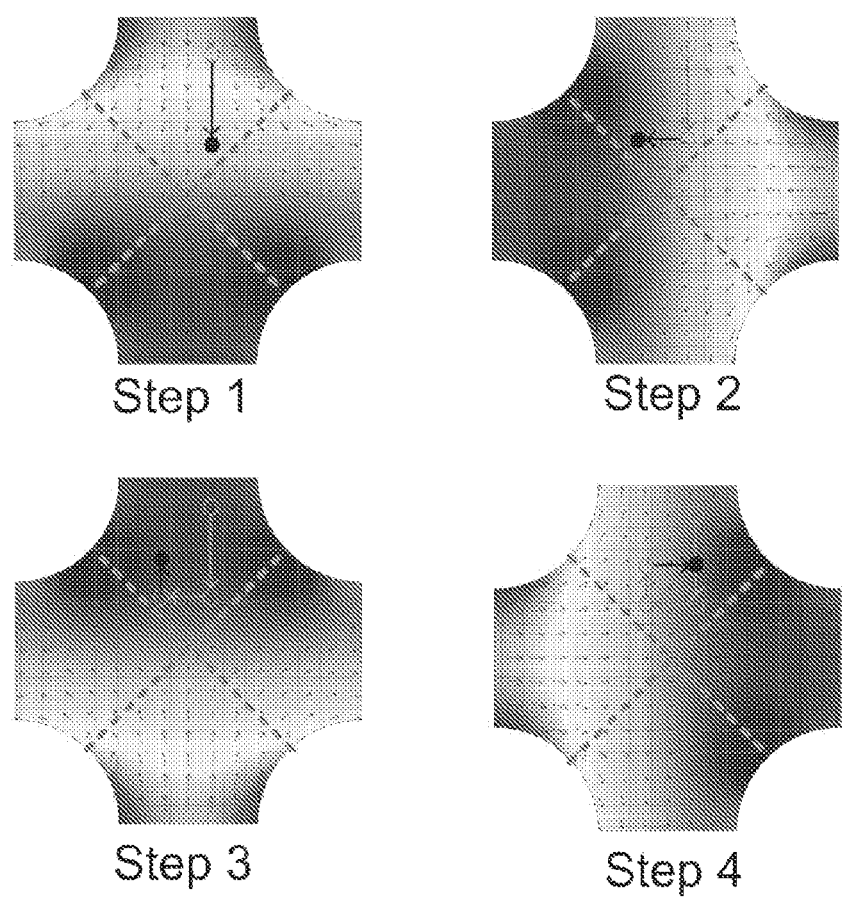
FIG. 6 shows stepwise rotation of the electric field leading to focusing of molecules whose mobility increases with temperature in one embodiment of affinity SCODA. A particle path is shown by the arrows.

In some embodiments, the electric field pattern of FIG. 5 is rotated in a stepwise manner by rotating the voltage pattern around the four electrodes such that the time averaged electric field is zero as shown in FIG. 6. This rotating field will result in net migration towards the centre of the gel for any molecule that is negatively charged and has a mobility that varies with temperature. In some embodiments, the electric field pattern is varied in a manner other than rotation, e.g. by sequentially shifting the voltage pattern by 180°, 90°, 180°, and 90°, or by randomly switching the direction of the electric field. As shown above, the mobility of a molecule moving through an affinity matrix depends on temperature, not electric field strength. The applied electric field will tend to increase the temperature of the matrix through Joule heating; the magnitude of the temperature rise at any given point in the matrix will be proportional to the square of the magnitude of the electric field.

In embodiments in which the thermal gradient is provided by Joule heating produced by the electric field that also provides the driving field, the oscillations in the thermal gradient will have the same period as the electric field oscillations. These oscillations can drive affinity SCODA based concentration in a two dimensional gel.

FIG. 6 illustrates the stepwise rotation of the electric field leading to focusing of molecules whose mobility increases with temperature or electric field according to such an embodiment. A particle path for a negatively charged molecule is shown. After four steps the particle has a net displacement toward the centre of the gel. Molecules that do not experience a change in mobility with changing temperature or electric field will experience zero net motion in a zero time averaged electric field.

Theoretical Predictions of Focusing and Separation

In some embodiments, the electric field and subsequently the Joule heating within an affinity SCODA gel are controlled by both the voltage applied to the source electrodes, and the shape of the gel. Marziali et al.[1] used superimposed rotating dipole and quadrupole fields to drive electrophoretic SCODA concentration. The ratio of the strength of these two fields, the dipole to quadrupole ratio (D/Q), has an impact on the efficiency of SCODA focusing with a maximum at around D/Q=4.5, however the optimum is relatively flat with the SCODA force staying relatively constant for values between 1.75 and 10[13]. One convenient choice of D/Q is 2. With this particular choice, only two distinct potentials need to be applied to the source electrodes, which can be achieved by connecting one electrode to a common voltage rail, grounding the other three, and rotating this pattern in a stepwise manner through the four possible configurations as shown in Table 1. Although analog amplifiers can be used and were used in the examples described herein, using a D/Q ratio of 2 allows one to use discrete MOSFET switches, which simplifies and reduces the required size and complexity of the power supplies.

TABLE 1

Voltage pattern for SCODA focusing with D/Q = 2.

| | Electrode A | Electrode B | Electrode C | Electrode D |
|---|---|---|---|---|
| Step 1 | −V | 0 | 0 | 0 |
| Step 2 | 0 | −V | 0 | 0 |
| Step 3 | 0 | 0 | −V | 0 |
| Step 4 | 0 | 0 | 0 | −V |

A starting point for a sequence specific gel geometry was the four-sided gel geometry used for the initial demonstration of electrophoretic SCODA. This geometry can be defined by two numbers, the gel width and the corner radius. The inventors started by using a geometry that had a width of 10 mm and a corner radius of 3 mm. An electro-thermal model of this geometry was implemented in COMSOL Multiphysics® modeling software (COMSOL, Inc, Burlington Mass., USA) to estimate the electric field and temperature profiles within the gel and establish whether or not those field and temperature profiles could drive concentration of a target with a temperature dependent mobility. The model used simultaneously solves Ohm's Law and the heat equation within the domain, using the power density calculated from the solution of Ohm's Law as the source term for the heat equation and using the temperature solution from the heat equation to determine the temperature dependent electrical conductivity of the electrolyte in the gel.

Figure 7:
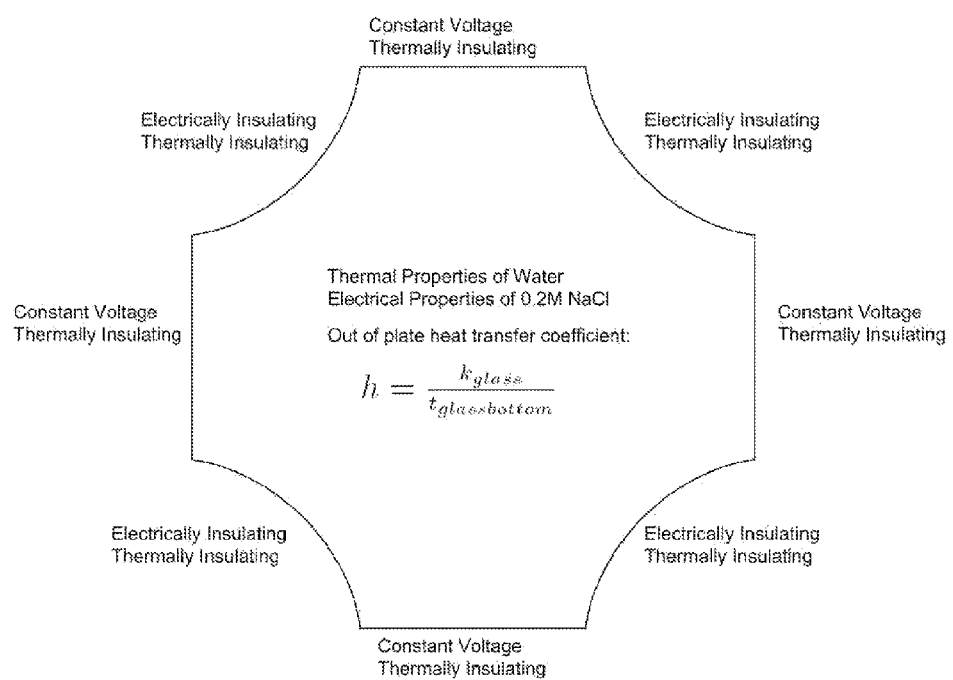
FIG. 7 shows the gel geometry including boundary conditions and bulk gel properties used for electrothermal modeling.
Figure 8:
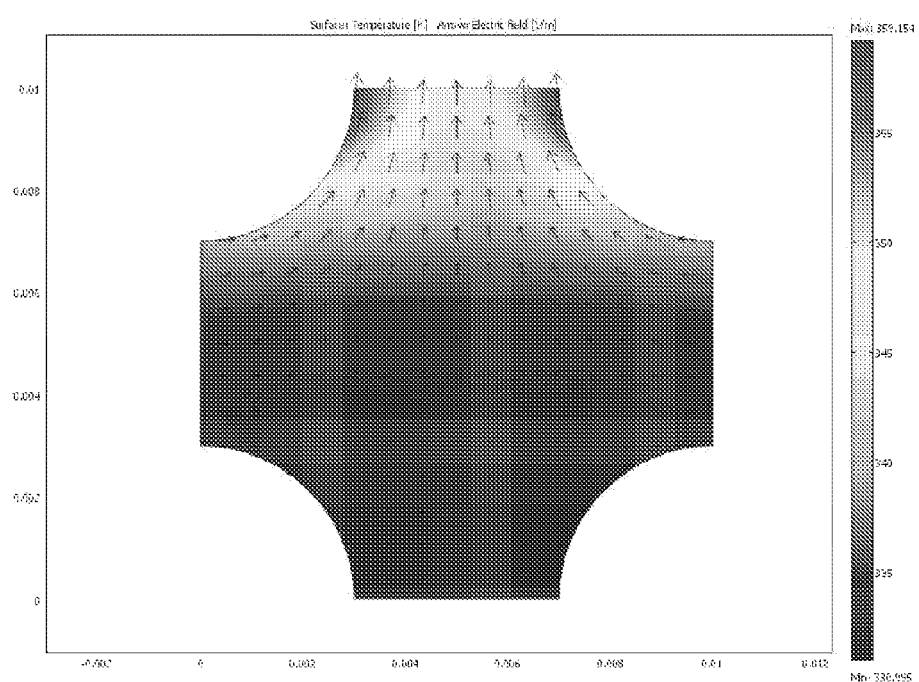
FIG. 8 shows the results of an electrothermal model for a single step of the SCODA cycle in one embodiment. Voltage applied to the four electrodes was −120 V, 0 V, 0 V, 0 V. Spreader plate temperature was set to 55° C. (328 K).

To obtain an accurate estimate of the temperature profile within the gel, the heat conducted out of the top and bottom of the gel are modeled. Boundary conditions and other model parameters are illustrated in FIG. 7. The thermal properties of water and electrical properties of 0.2 M NaCl were used. The gel cassettes are placed on an aluminum spreader plate that acts as a constant temperature reservoir. To model heat flow into the spreader plate the heat transfer coefficient of the glass bottom, given by lilt, was used. The temperature and electric field profiles solved by this model for a single step of the SCODA cycle are shown in FIG. 8. The voltage applied to the four electrodes was −120 V, 0 V, 0 V, 0 V, and the spreader plate temperature was set to 55° C. (328 K). The colour map indicates gel temperature and the vector field shows the relative magnitude and direction of the electric field within the gel. Note that as DNA is negatively charged its migration direction will be opposite to the direction of the electric field.

Using experimentally determined values of mobility versus temperature for a given molecule and the thermal model described above, it is possible to determine the SCODA velocity everywhere in the gel for that particular molecule by taking the time average of the instantaneous drift velocity integrated over one complete cycle:

$$\vec{v}_s = \frac{1}{\tau}\int_0^\tau \mu(T(\vec{r}, t))\vec{E}(\vec{r}, t)dt \quad [33]$$

where μ is the temperature dependent mobility, E the electric field and τ the period of the SCODA cycle. The temperature and electric field were solved for four steps in the SCODA cycle and coupled with the mobility function in equation [23]. In this manner, the SCODA velocity everywhere in the gel can be calculated. Since discrete steps are being used, if it is assumed that the period is long enough that the phase lag between the electric field and temperature can be neglected, then the integral in equation [33] becomes a sum:

$$\vec{v}_s = \frac{\sum \mu(T_i(\vec{r}))\vec{E}_i(\vec{r})t_i}{\sum t_i} \quad [34]$$

where the velocity is summed over all four steps in the cycle.

Figure 9:
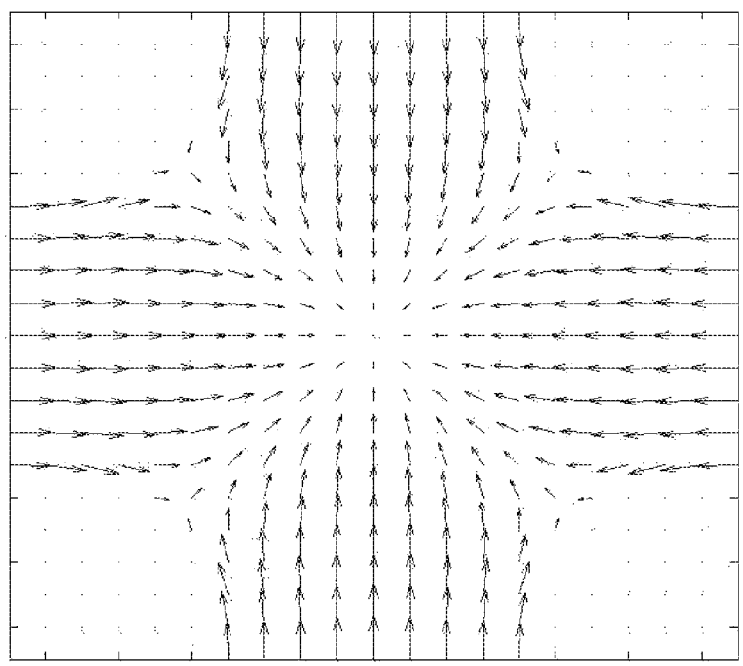
FIG. 9 shows SCODA velocity vector plots in one exemplary embodiment of the invention.

As an example, FIG. 9 shows a vector plot of the SCODA velocity using the experimentally determined mobility versus temperature curve for the perfect match target shown in FIG. 11 (example described below) and the temperature and electric field values calculated above.

The velocity field plotted in FIG. 9 shows a zero velocity point at the geometric centre of the gel, with the velocity at all other points in the gel pointing towards the centre. Thus, target molecules can be collected within the gel at the centre of the electric field pattern.

In embodiments that are used to separate two similar molecules based on differences in binding affinity for the immobilized probe, a washing force is superimposed over the SCODA focusing fields described above. In some embodiments, the washing force is a DC electric field, described herein as a DC bias. For molecules having affinity to the immobilized probe, the SCODA focusing force applied by the SCODA focusing fields described above will tend to counteract movement of a molecule caused by the washing field, i.e. the SCODA focusing fields will tend to exert a restoring force on the molecules and the molecules will be preferentially focused as compared with molecules having a smaller binding affinity. Molecules that have a smaller binding affinity to the immobilized probe will have a greater mobility through the affinity matrix, and the restoring SCODA force will be weaker. As a result, the focus spot of molecules with a smaller binding affinity will be shifted. In some cases, the restoring SCODA force will be so weak that such molecules with a smaller binding affinity will be washed out of the affinity matrix altogether.

In order to enrich for a specific biomolecule from a population of other similar biomolecules using affinity SCODA, one may operate SCODA focusing electric fields with a superimposed DC bias. The DC bias may move the focused molecules off centre, in such a way that the molecules with a lower binding energy to the immobilized binding sites move further off centre than the molecules with higher binding energies, thus causing the focus to split into multiple foci. For molecules with similar binding energies, this split may be small while washing under bias. The DC bias may be superimposed directly over the focusing fields, or a DC field may be time multiplexed with the focusing fields.

In one exemplary embodiment used to separate nucleic acids having similar sequences, a DC bias is superimposed over the voltage pattern shown in Table 1, resulting in the voltage pattern shown below in Table 2. In some embodiments, the DC bias is applied alternately with the SCODA focusing fields, i.e. the SCODA focusing fields are applied for a period of time then stopped, and the DC bias is applied for a period of time then stopped.

TABLE 2

Applied voltages for focusing under a DC bias. Shown are values for a 120 V SCODA focusing potential superimposed over a 10 V DC bias.

| | Electrode A | Electrode B | Electrode C | Electrode D |
|---|---|---|---|---|
| Step 1 | −120 | 5 | 10 | 5 |
| Step 2 | 0 | −115 | 10 | 5 |
| Step 3 | 0 | 5 | −110 | 5 |
| Step 4 | 0 | 5 | 10 | −115 |

Figure 10A:
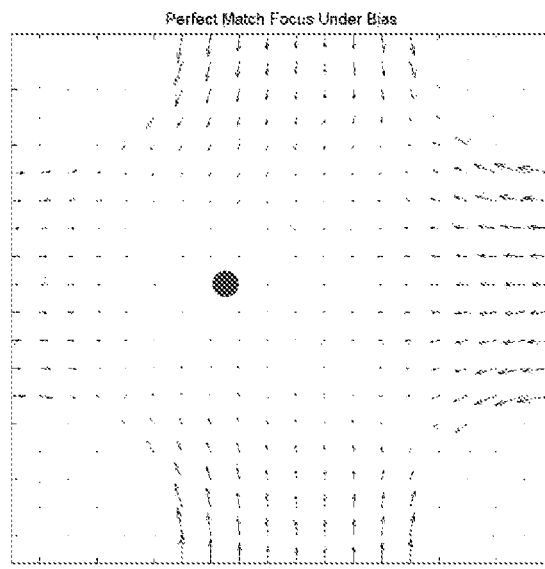
FIGS. 10A and 10B show predictions of SCODA focusing under the application of a DC washing bias in one embodiment.
Figure 10B:
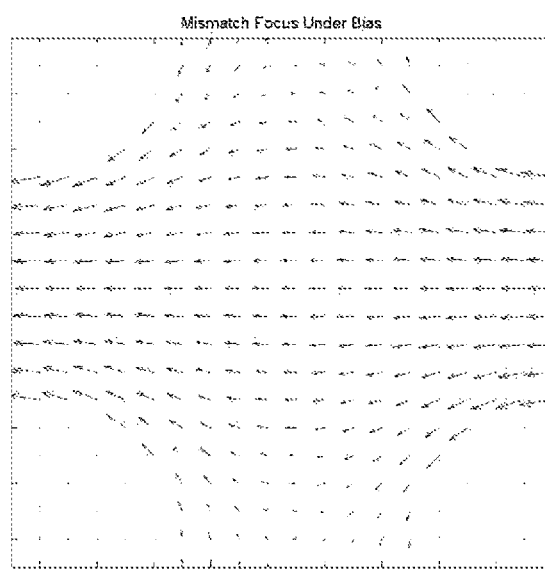

The resulting velocity plots of both the perfect match and single base mismatch targets in the presence of the applied DC bias are shown in FIGS. 10A and 10B, respectively. Electric field and temperature were calculated using COMSOL using a spreader plate temperature of 61° C. Velocity was calculated using equation [34] and the experimentally obtained data fits shown in FIG. 11 (example described below). The zero velocity location of the perfect match target has been moved slightly off centre in the direction of the bias (indicated with a circular spot), however the mismatch target has no zero velocity point within the gel. These calculations show that it is possible to completely wash a target with a smaller binding affinity from the immobilized probe from the gel area while capturing the target with a higher binding affinity, enabling selective purification, concentration and/or detection of a specific sequence, even where the nucleotide targets differ in sequence at only one position.

In some embodiments, the optimal combination of the driving field and the mobility altering field used to perform SCODA focusing where there is a maximum difference in focusing force between similar molecules is empirically determined by measuring the velocity of sample molecules through a medium as a function of the mobility varying field. For example, in some embodiments the mobility of a desired target molecule and a non-desired target molecule at various temperatures is measured in an affinity matrix as described above, and the temperature range at which the difference in relative mobility is greatest is selected as the temperature range for conducting affinity SCODA. In some embodiments, the focusing force is proportional to the rate at which the velocity changes with respect to the perturbing field $dv/df$, where v is the molecule velocity and f the field strength. One skilled in the art may maximize $dv/df$ so as to maximize SCODA focusing and to enable fast washing of contaminants that do not focus. To maximally separate two similar molecules, affinity SCODA may be carried out under conditions such that $dv_a/df - dv_b/df$ (where $v_a$ is the velocity of molecule a, and $v_b$ is the velocity of molecule b) is maximized.

In some embodiments, the strength of the electric field applied to an affinity matrix is calculated so that the highest temperature within the gel corresponds approximately to the temperature at which the difference in binding affinity between two molecules to be separated is highest.

In some embodiments, the temperature at which the difference in binding affinity between the two molecules to be separated is highest corresponds to the temperature at which the difference between the melting temperature of a target molecule and the affinity agent and the melting temperature of a non-target molecule and the affinity agent is highest. In some embodiments, the maximum difference between the melting temperature of a target molecule and the affinity agent and the melting temperature of a non-target molecule and the affinity agent is less than about 9.3° C., in some embodiments less than about 7.8° C., in some embodiments less than about 5.2° C., and in some embodiments less than about 0.7° C.

In some embodiments, the ratio of target molecules to non-target molecules that can be separated by affinity SCODA is any ratio from 1:1 to 1:10,000 and any value therebetween, e.g. 1:100 or 1:1,000. In some embodiments, after conducting affinity SCODA, the ratio of non-target molecules relative to target molecules that is located in a focus spot of the target molecules has been reduced by a factor of up to 10,000 fold.

Phase Lag Induced Rotation

In some embodiments, to separate molecules with different affinities for the immobilized affinity agent, a DC bias is superimposed over the SCODA focusing fields as described above. If the separation in binding energy is great enough then the mismatched target can be washed entirely off of the gel. The ability to wash weakly focusing contaminating fragments from the gel can be affected by the phase lag induced rotation discussed above, where the SCODA velocity of a two dimensional system was given by:

$$\vec{v}_{SCODA} = |v_{SCODA}|(\cos(\phi)\hat{r} + \sin(\phi)\hat{\theta}) \quad [35]$$

where $\phi$ is the phase lag between the electric field oscillations and the mobility varying oscillations. Aside from reducing the proportion of the SCODA velocity that contributes to concentration this result has additional implications when washing weakly focusing contaminants out of an affinity matrix. The rotational component will add to the DC bias and can result in zero or low velocity points in the gel that can significantly increase the time required to wash mismatched targets from the gel.

To counteract the effects of a rotational component of motion that may arise in embodiments in which there is a phase lag between the electric field oscillations and the mobility varying oscillations, the direction in which the SCODA focusing fields are applied may be rotated periodically. In some embodiments, the direction in which the SCODA focusing fields are rotated is altered once every period.

Optical Feedback

In some embodiments where one molecule of interest (the target molecule) is concentrated in an affinity matrix while a second, similar, molecule (the non-target molecule) is washed off of the affinity matrix, optical feedback may be used to determine when washing is complete and/or to avoid running the target molecule out of the affinity matrix.

The two foci of similar molecules may be close together geographically, and optical feedback may be used to ensure the molecule of interest is not washed off the gel. For example, using a fluorescent surrogate for the molecule of interest or the contaminating molecules (or both) one can monitor their respective positions while focusing under bias, and use that geographical information to adjust the bias ensuring that the molecule of interest is pushed as close to the edge of the gel as possible but not off, while the contaminating molecule may be removed from the gel.

In some embodiments, the molecules to be separated are differentially labeled, e.g. with fluorescent tags of a different colour. Real-time monitoring using fluorescence detection can be used to determine when the non-target molecule has been washed off of the affinity matrix, or to determine when the foci of the target molecule and the non-target molecule are sufficiently far apart within the affinity matrix to allow both foci to be separately extracted from the affinity matrix.

In some embodiments, fluorescent surrogate molecules that focus similarly to the target and/or non-target molecules may be used to perform optical feedback. By using a fluorescent surrogate for a target molecule, a non-target molecule, or both a target molecule and a non-target molecule, the respective positions of the target molecule and/or the non-target molecule can be monitored while performing affinity focusing under a washing bias. The location of the surrogate molecules within the affinity matrix can be used to adjust the washing bias to ensure that the molecule of interest is pushed as close to the edge of the gel as possible but not off, while the contaminating molecule may be washed off the gel.

In some embodiments, fluorescent surrogate molecules that focus similarly to the target and/or non-target molecules but will not amplify in any subsequent PCR reactions that may be conducted can be added to a sample to be purified. The presence of the fluorescent surrogate molecules within the affinity matrix enables the use of optical feedback to control SCODA focusing conditions in real time. Fluorescence detection can be used to visualize the position of the fluorescent surrogate molecules in the affinity matrix. In embodiments where the fluorescent surrogate mimics the focusing behaviour of the target molecule, the applied washing force can be decreased when the fluorescent surrogate approaches the edge of the affinity matrix, to avoid washing the target molecule out of the affinity matrix. In embodiments where the fluorescent surrogate mimics the focusing behaviour of the non-target molecule that is to be separated from the target molecule, the applied washing force can be decreased or stopped after the fluorescent surrogate has been washed out of the affinity matrix, or alternatively when the location of the fluorescent surrogate approaches the edge of the affinity matrix.

Separation of Differentially Modified Molecules

In some embodiments, molecules that are identical except for the presence or absence of a chemical modification that alters the binding affinity of the molecule for a probe are separated using affinity SCODA. Some embodiments of affinity SCODA are sufficiently sensitive to separate two molecules that have only a small difference in binding affinity for the immobilized affinity agent. Examples of such molecules include differentially modified molecules, such as methylated and unmethylated nucleic acids, methylated or acetylated proteins, or the like.

For example, it has been previously shown that methylation of cytosine residues increases the binding energy of hybridization relative to unmethylated DNA sequences. RNA sequences would be expected to display a similar increase in the binding energy of hybridization when methylated as compared with unmethylated sequences. The inventors have shown that one embodiment of affinity SCODA can be used to separate nucleic acid sequences differing only by the presence of a single methylated cytosine residue. Other chemical modifications would be expected to alter the binding energy of a nucleic acid and its complimentary sequence in a similar manner. Modification of proteins, such as through methylation, can also alter the binding affinity of a protein of interest with a protein, RNA or DNA aptamer, antibody, or other molecule that binds to the protein at or near the methylation site. Accordingly, embodiments of affinity SCODA can be used to separate differentially modified molecules of interest. While the examples herein are directed to methylation enrichment, affinity SCODA can also be applied to enrichment and selection of molecules with other chemical differences, including e.g. acetylation.

Affinity SCODA, and sequence-specific SCODA, may be used to enrich a specific sequence of methylated DNA out of a background of methylated and unmethylated DNA. In this application of affinity SCODA, the strength of the SCODA focusing force may be related to the binding energy of the target DNA to the bound oligonucleotides. Target molecules with a higher binding energy may be made to focus more strongly than targets with lower binding energy. Methylation of DNA has previously been documented to slightly increase the binding energy of target DNA to its complementary sequence. Small changes in binding energy of a complementary oligonucleotide may be exploited through affinity SCODA to preferentially enrich for methylated DNA. SCODA operating conditions may be chosen, for example as described above, such that the methylated DNA is concentrated while unmethylated DNA of the same sequence is washed off the gel.

Some embodiments can separate molecules with a difference in binding energy to an immobilized affinity agent of less than kT, the thermal excitation energy of the target molecules. Some embodiments can separate molecules with a difference in binding energy to an immobilized affinity agent of less than 0.19 kcal/mol. Some embodiments can separate molecules with a difference in binding energy to an immobilized affinity agent of less than 2.6 kcal/mol. Some embodiments can separate molecules with a difference in binding energy to an immobilized affinity agent of less than 3.8 kcal/mol. Some embodiments can separate molecules that differ only by the presence of a methyl group. Some embodiments can separate nucleic acid sequences that differ in sequence at only one base.

Applications of Affinity SCODA

Systems and methods for separating, purifying, concentrating and/or detecting differentially modified molecules as described above can be applied in fields where detection of biomarkers, specific nucleotide sequences or differentially modified molecules is important, e.g. epigenetics, fetal DNA detection, pathogen detection, cancer screening and monitoring, detection of organ failure, detection of various disease states, and the like. For example, in some embodiments affinity SCODA is used to separate, purify, concentrate and/or detect differentially methylated DNA in such fields as fetal diagnostic tests utilizing maternal body fluids, pathogen detection in body fluids, and biomarker detection in body fluids for detecting cancer, organ failure, or other disease states and for monitoring the progression or treatment of such conditions.

In some embodiments, a sample of bodily fluid or a tissue sample is obtained from a subject. Cells may be lysed, genomic DNA is sheared, and the sample is subjected to affinity SCODA. In some embodiments, molecules concentrated using affinity SCODA are subjected to further analysis, e.g. DNA sequencing, digital PCR, fluorescence detection, or the like, to assay for the presence of a particular biomarker or nucleotide sequence. In some embodiments, the subject is a human.

It is known that fetal DNA is present in maternal plasma, and that differential methylation of maternal versus fetal DNA obtained from the maternal plasma can be used to screen for genetic disorders (see e.g. Poon et al., 2002, *Clinical Chemistry* 48:1, 35-41). However, one problem that is difficult to overcome is discrimination between fetal and maternal DNA. Affinity SCODA as described above may be used to preferentially separate, purify, concentrate and/or detect DNA which is differentially methylated in fetal DNA versus maternal DNA. For example, affinity SCODA may be used to concentrate or detect DNA which is methylated in the fetal DNA, but not in maternal DNA, or which is methylated in maternal DNA but not fetal DNA. In some embodiments, a sample of maternal plasma is obtained from a subject. and subjected to affinity SCODA using an oligonucleotide probe directed to a sequence of interest. The detection of two foci after the application of SCODA focusing fields may indicate the presence of DNA which is differentially methylated as between the subject and the fetus. Comparison to a reference sample from a subject that exhibits a particular genetic disorder may be used to determine if the fetus may be at risk of having the genetic disorder. Further analysis of the sample of DNA obtained through differential modification SCODA through conventional methods such as PCR, DNA sequencing, digital PCR, fluorescence detection, or the like, may be used to assess the risk that the fetus may have a genetic disorder.

One embodiment of the present systems and methods is used to detect abnormalities in fetal DNA, including chromosome copy number abnormalities. Regions of different chromosomes that are known to be differentially methylated in fetal DNA as opposed to maternal DNA are concentrated using affinity SCODA to separate fetal DNA from maternal DNA based on the differential methylation of the fetal DNA in a maternal plasma sample. Further analysis of the separated fetal DNA is conducted (for example using qPCR, DNA sequencing, fluorescent detection, or other suitable method) to count the number of copies from each chromosome and determine copy number abnormalities.

Most cancers are a result of a combination of genetic changes and epigenetic changes, such as changes in DNA methylation (e.g. hypomethylation and/or hypermethylation of certain regions, see e.g. Ehrich, 2002, *Oncogene* 21:35, 5400-5413). Affinity SCODA can be used to separate, purify, concentrate and/or detect DNA sequences of interest to screen for oncogenes which are abnormally methylated. Embodiments of affinity SCODA are used in the detection of biomarkers involving DNA having a different methylation pattern in cancerous or pre-cancerous cells than in healthy cells. Detection of such biomarkers may be useful in both early cancer screening, and in the monitoring of cancer development or treatment progress. In some embodiments, a sample obtained from a subject, e.g. a sample of a bodily fluid such as plasma or a biopsy, may be processed and analyzed by differential modification SCODA using oligonucleotide probes directed to a sequence of interest. The presence of two foci during the application of SCODA fields may indicate the presence of differential methylation at the DNA sequence of interest. Comparison of the sample obtained from the subject with a reference sample (e.g. a sample from a healthy patient and/or a sample known to originate from cancerous or pre-cancerous tissue) can indicate whether the cells of the subject are at risk of being cancerous or pre-cancerous. Further analysis of the sample of DNA obtained through differential modification SCODA through conventional methods such as PCR, DNA sequencing, digital PCR, fluorescence detection, or the like, may be used to assess the risk that the sample includes cells that may be cancerous or pre-cancerous, to assess the progression of a cancer, or to assess the effectiveness of treatment.

In some embodiments, a specific nucleotide sequence is captured in the gel regardless of methylation (i.e. without selecting for a particular methylation status of the nucleic acid). Undesired nucleotide sequences and/or other contaminants may be washed off the gel while the specific nucleotide sequence remains bound by oligonucleotide probes immobilized within the separation medium. Then, differential methylation SCODA is used to focus the methylated version of the sequence while electrically washing the unmethylated sequence toward a buffer chamber or another gel where it can then be recovered. In some embodiments, the unmethylated sequence could be preferentially extracted.

In some embodiments, biomolecules in blood related to disease states or infection are selectively concentrated using affinity SCODA. In some embodiments, the biomolecules are unique nucleic acids with sequence or chemical differences that render them useful biomarkers of disease states or infection. Following such concentration, the biomarkers can be detected using PCR, sequencing, or similar means. In some embodiments, a sample of bodily fluid or tissue is obtained from a subject, cells are lysed, genomic DNA is sheared, and affinity SCODA is performed using oligonucleotide probes that are complimentary to a sequence of interest. Affinity SCODA is used to detect the presence of differentially methylated populations of the nucleic acid sequence of interest. The presence of differentially methylated populations of the target sequence of interest may indicate a likelihood that the subject suffers from a particular disease state or an infection.

In some embodiments, the focusing pattern of the target nucleic acid produced by affinity SCODA from a subject is compared with the focusing pattern of the target nucleic acid produced by affinity SCODA from one or more reference samples (e.g. an equivalent sample obtained from a healthy subject, and/or an equivalent sample obtained from a subject known to be suffering from a particular disease). Similarities between the focusing pattern produced by the sample obtained from the subject and a reference sample obtained from a subject known to be suffering from a particular disease indicate a likelihood that the subject is suffering from the same disease. Differences between the focusing pattern produced from the sample obtained from the subject and a reference sample obtained from a healthy subject indicate a likelihood that the subject may be suffering from a disease. Differences in the focusing pattern produced from the sample obtained from the subject and a reference sample obtained from a healthy subject may indicate the presence of a differential modification or a mutation in the subject as compared with the healthy subject.

Use of Multiple Affinity Agents to Capture Multiple Target Molecules

In some embodiments, affinity SCODA is used to separate, purify, concentrate and/or detect more than one sequence per sample. The examples described herein demonstrate that it is possible to concentrate target DNA at probe concentrations as low as 1 µM, as well as with probe concentrations as high as 100 µM. In some embodiments, multiplexed concentration is be performed by immobilizing a plurality of different affinity agents in the medium to provide an affinity matrix. In some embodiments, at least two different affinity agents are immobilized within a medium to separate, purify, concentrate and/or detect at least two different target molecules. In some embodiments, each one of the affinity agents is an oligonucleotide probe with a different sequence. In some embodiments, anywhere between 2 and 100 different oligonucleotide probes are immobilized within a medium to provide an affinity matrix, and any where between 2 and 100 different target molecules are separated, purified, concentrated and/or detect simultaneously in a single affinity gel. Each one of the target molecules may be labeled with a different tag to facilitate detection, for example each one of the target molecules could be labeled with a different colour of fluorescent tag.

In some embodiments where the binding energy between each of the two or more affinity agents and the two or more target molecules differs, the two or more target molecules may be differentially separated within the affinity matrix by the application of SCODA focusing fields at an appropriate temperature. In some embodiments, a first target molecule with a lower melting temperature for its corresponding affinity agent may be preferentially separated from a second target molecule with a relatively higher melting temperature for its corresponding affinity agent. In some such embodiments, the first molecule is preferentially concentrated by conducting SCODA focusing at a temperature that is sufficiently low that a second target molecule with a relatively higher melting temperature for its corresponding affinity agent does not focus efficiently (i.e. a temperature at which the mobility of the second target molecule within the affinity matrix is relatively low), but sufficiently high to enable efficient focusing of the first molecule. In some such embodiments, the first and second molecules are differentially separated through the application of a washing bias, e.g. a DC bias, at a temperature that is sufficiently low that the second target molecule is not displaced or is displaced only slowly by the washing bias, but sufficiently high that the first target molecule is displaced or is displaced at a higher velocity by the washing bias.

Apparatus for Performing Affinity SCODA

In some embodiments, affinity SCODA is performed on an electrophoresis apparatus comprising a region for containing the affinity matrix, buffer reservoirs, power supplies capable of delivering large enough voltages and currents to cause the desired effect, precise temperature control of the SCODA medium (which is a gel in some embodiments), and a two colour fluorescence imaging system for the monitoring of two different molecules in the SCODA medium.

EXAMPLES

Embodiments of the invention are further described with reference to the following examples, which are intended to be illustrative and not restrictive in nature. Although the examples below are described with reference to the separation of DNA oligonucleotides and methylated DNA oligonucleotides, embodiments of the present invention also have application in the purification and separation of other molecules having an affinity for agents immobilized within a medium, including other differentially modified molecules. Examples of such molecules include polypeptides or proteins, differentially modified polypeptides or proteins, differentially modified nucleic acids including differentially methylated DNA or RNA, or the like. Examples of agents that can be immobilized as probes in embodiments of the invention include DNA, RNA, antibodies, polypeptides, proteins, nucleic acid aptamers, and other agents with affinity for a molecule of interest.

Example 1.0

Affinity SCODA with Single Base Mismatch

To verify the predicted temperature dependent mobility expressed in equation [23], experiments were performed to measure the response of target DNA velocity to changes in temperature. Initial experiments were done with 100 nucleotide oligonucleotides as target DNA. Oligonucleotides are single stranded so do not need to be denatured to interact with the affinity gel. The oligonucleotides are also sufficiently short that they have a negligible field dependent mobility. Longer nucleic acid molecules, e.g. greater than about 1000 nucleotides in length, may be difficult to separate based on sequence, as longer molecules have a tendency to focus in a non-sequence specific manner from the electrophoretic SCODA effect in embodiments using Joule heating provided by an electric field to provide the temperature gradient.

To perform these measurements a polyacrylamide gel (4% T, 2% C) in 1×TB (89 mM tris, 89 mM boric acid) with 0.2 M NaCl and 10 µM acrydite probe (SEQ ID NO. 1) oligo was cast in a one dimensional gel cassette containing only two access ports. Polymerization was initiated through the addition of 2 µl of 10% w/v APS and 0.2 µl TEMED per ml of gel.

Mobility measurements were performed on two different 100 nucleotide oligonucleotides differing by a single base containing sequences with a perfect match (PM) (SEQ ID NO. 2) to the probe and a single base mismatch (sbMM) (SEQ ID NO. 3). These target oligonucleotides were end labeled with either 6-FAM or Cy5 (IDT DNA). Probe and target sequences used for these experiments are shown in Table 3. The regions of the PM and sbMM target oligonucleotides that are complementary to the immobilized probe are shown in darker typeface than the other portions of these oligonucleotides. The position of the single base mismatch is underlined in the sbMM target sequence.

TABLE 3

Probe and target oligonucleotide sequences used for sequence specific SCODA.

| | Sequence |
|---|---|
| Probe (SEQ ID NO.: 1) | 5' ACT GGC CGT CGT TTT ACT 3' |

TABLE 3-continued

Probe and target oligonucleotide sequences used for sequence specific SCODA.

| | Sequence |
|---|---|
| PM Target (SEQ ID NO.: 2) | 5' CGA TTA AGT TGA GTA ACG CCA CTA TTT TCA CAG TCA TAA CCA TGT AAA ACG ACG GCC AGT GAA TTA GCG ATG CAT ACC TTG GGA TCC TCT AGA ATG TAC C 3' |
| sbMM Target (SEQ ID NO.: 3) | 5' CGA TTA AGT TGA GTA ACG CCA CTA TTT TCA CAG TCA TAA CCA TGT AAA ACT ACG GCC AGT GAA TTA GCG ATG CAT ACC TTG GGA TCC TCT AGA ATG TAC C 3' |

The probe sequence was chosen to be complementary to pUC19 for subsequent experiments with longer targets, discussed below. The 100 nucleotide targets contain a sequence complementary to the probe (perfect match: PM) or with a single base mismatch (sbMM) to the probe with flanking sequences to make up the 100 nucleotide length. The flanking sequences were designed to minimize the effects of secondary structure and self hybridization. Initial sequences for the regions flanking the probe binding site were chosen at random. Folding and self hybridization energies were then calculated using Mfold[14] and the sequences were altered one base at a time to minimize these effects ensuring that the dominant interactions would be between target strands and the probe.

Table 4 shows the binding energies and melting temperatures for the sequences shown in Table 3 calculated using Mfold. The binding energy, $\Delta G$, is given as $\Delta H - T\Delta S$, where $\Delta H$ is the enthalpy and $\Delta S$ the entropy in units of kcal/mol and kcal/mol K respectively. The following parameter values were used for calculation of the values in Table 2: temperature=50° C., [Na+]=0.2 M, [Mg++]=0 M, strand concentration=10 µM. The largest $T_m$ for non probe-target hybridization is 23.9° C. and the greatest secondary structure $T_m$ is 38.1° C. Both of these values are far enough below the sbMM target-probe $T_m$ that they are not expected to interfere target-probe interactions.

Once the injected band was visible the temperature of the spreader plate was dropped to 55° C. An electric field of 25 V/cm was applied to the gel cassette while the temperature was ramped from 40° C. to 70° C. at a rate of 0.5° C./min. Images of the gel were taken every 20 sec. Image processing software written in LabView® (National Instruments, Austin Tex.) was used to determine the location of the centre of the band in each image and this position data was then used to calculate velocity.

Figure 11:
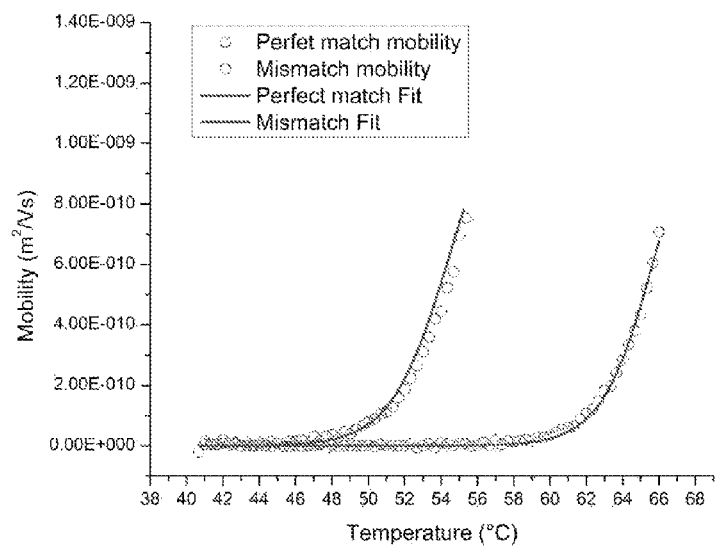
FIG. 11 shows the results of the measurement of temperature dependence of DNA target mobility through a gel containing immobilized complementary oligonucleotide probes for one exemplary separation.

FIG. 11 shows a plot of target DNA mobility as a function of temperature. Using the values of $\Delta G$ for the probe and target sequences shown in Table 3, the velocity versus temperature curves were fit to equation [23] to determine the two free parameters: the mobility $\mu_0$, and $\beta$ a constant that depends on the kinetics of the hybridization reaction.

A fit of the data shown in FIG. 11 shows good agreement with the theory of migration presented above. Data for the mismatch mobility are shown as the curve on the left, and data for the perfect match mobility are shown as the curve on the right. The $R^2$ value for the PM fit and MM fits were 0.99551 and 0.99539 respectively. The separation between the perfect match and single base mismatch targets supports that there is an operating temperature where the focusing speed of the perfect match target is significantly greater than that of the mismatched target enabling separation of the two species through application of a DC bias field as illustrated in FIG. 4.

Example 2.0

Selective Separation of Molecules Using Affinity SCODA

A 4% polyacrylamide gel containing 10 µM acrydite modified probe oligos (Integrated DNA Technologies, www.idtdna.com) was cast in a gel cassette to provide an affinity matrix.

Equimolar amounts of the perfect match and single base mismatch targets were injected into the affinity gel at 30° C. with an electric field of 100 V/cm applied across the gel such that both target molecules would be initially captured and immobilized at the gel buffer interface. The temperature was then increased to 70° C. and a constant electric field of 20 V/cm applied to the gel to move the target into the imaging area of the gel. The temperature was then dropped to 62° C. and a 108 V/cm SCODA focusing field superimposed over

TABLE 4

Binding energies and melting temperatures for Table 3 sequences.

| | Probe (SEQ ID NO.: 1) | PM Target (SEQ ID NO.: 2) | sbMM Target (SEQ ID NO.: 3) | Secondary Structure |
|---|---|---|---|---|
| Probe (SEQ ID NO.: 1) | −35.4 + 0.1012 * T Tm = 12.2° C. | −145.3 + 0.4039 * T Tm = 65.1° C. | −126.8 + 0.3598 * T Tm = 55.8° C. | −20.3 + 0.07049 * T Tm = 14.8° C. |
| PM Target (SEQ ID NO.: 2) | −145.3 + 0.4039 * T Tm = 65.1° C. | −40.2 + 0.1124 * T Tm = 23.9° C. | −40.2 + 0.1111 * T Tm = 20.9° C. | −24.3 + 0.07808 * T Tm = 38.1° C. |
| sbMM Target (SEQ ID NO.: 3) | −126.8 + 0.3598 * T Tm = 55.8° C. | −40.2 + 0.1111 * T Tm = 20.9° C. | −40.2 + 0.1124 * T Tm = 23.9° C. | −24.3 + 0.07808 * T Tm = 38.1° C. |

To measure the velocity response as a function of temperature the fluorescently labeled target was first injected into the gel at high temperature (70° C.), and driven under a constant electric field into the imaging area of the gel.

an 8 V/cm DC bias as shown in Table 2 was applied to the four source electrodes with a period of 5 seconds. The rotation direction of the SCODA focusing field was altered every period.

TABLE 5

Focusing plus bias potentials applied.

| | Electrode A | Electrode B | Electrode C | Electrode D |
|---|---|---|---|---|
| Step 1 | −108 | 4 | 8 | 4 |
| Step 2 | 0 | −104 | 8 | 4 |
| Step 3 | 0 | 4 | −100 | 4 |
| Step 4 | 0 | 4 | 8 | −104 |

Figure 12:
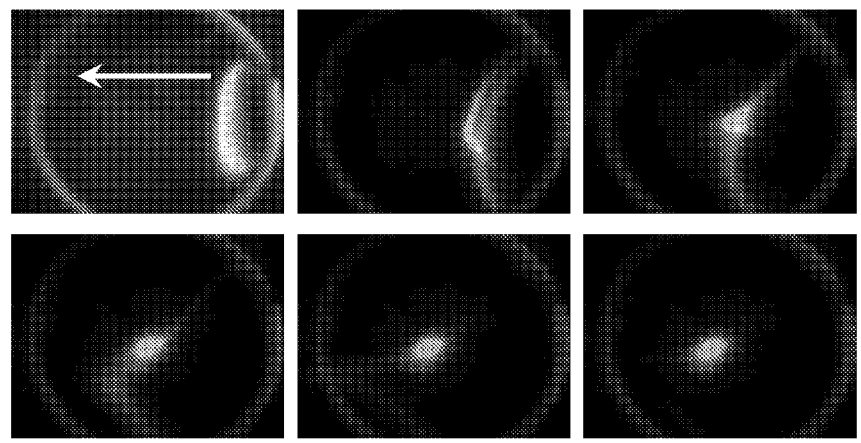
FIG. 12 shows a time series of affinity SCODA focusing under the application of DC bias according to one embodiment. Perfect match DNA is tagged with 6-FAM (green) (leading bright line that focuses to a tight spot) and single base mismatch DNA is tagged with Cy5 (red) (trailing bright line that is washed from the gel). Images taken at 3 minute intervals. The first image was taken immediately following injection.

FIG. 12 shows images of concentration taken every 2 minutes. The perfect match target was tagged with 6-FAM and shown in green (leading bright spot which focuses to a tight spot), the mismatch target was tagged with Cy5 and is shown in red (trailing bright line that is washed from the gel). The camera gain was reduced on the green channel after the first image was taken. DNA was injected into the right side of the gel and focusing plus bias fields were applied. The perfect match target (green) experiences a drift velocity similar to that shown in FIG. 10A and moves towards a central focus location. The more weakly focusing mismatch target (red) experiences a velocity field similar to that shown in FIG. 10B and is pushed off the edge of the gel by the bias field. The direction of application of the applied washing field is indicated by the white arrow.

This experiment verifies the predictions of FIGS. 10A and 10B demonstrating that it is possible to generate two different velocity profiles for two DNA targets differing by only a single base enabling preferential focusing of the target with the higher binding energy to the gel. The images in FIG. 12 confirm that there are two distinct velocity profiles generated for the two different sequences of target DNA moving through an affinity matrix under the application of both a SCODA focusing field and a DC bias. A dispersive velocity field is generated for the single base mismatch target and a non dispersive velocity field is generated for the perfect match target. This example demonstrates that it is possible to efficiently enrich for targets with single base specificity, and optionally wash a non-desired target off of an affinity matrix, even if there is a large excess of mismatch target in the sample.

Example 3.0

Optimization of Operating Conditions

Different parameters of the SCODA process may be optimized to achieve good sample enrichment at reasonable yields. In embodiments having immobilized (and negatively charged) DNA in the gel, a relatively high salinity running buffer was found to provide both efficient and stable focusing, as well as minimizing the time required to electrokinetically inject target DNA from an adjacent sample chamber into the SCODA gel.

Example 3.1

Optimization of Buffer Salinity

Early attempts of measuring the temperature dependent mobility of molecules in an affinity gel as well as the first demonstrations of sequence specific SCODA were performed in buffers used for electrophoretic SCODA. These are typically standard electrophoresis buffers such as tris-borate EDTA (TBE), often diluted 4 to 6 fold to reduce the gel conductivity, enabling the application of high electric fields within thermal limitations imposed by Joule heating, resulting in shorter concentration times[13]. Although it is possible to achieve sequence specific SCODA based concentration in a 1×TBE buffer (89 mM tris, 89 mM boric acid, 2 mM disodium EDTA), conditions can be further optimized for performance of sequence specific SCODA due to the relatively low concentration of dissociated ions at equilibrium in 1×TBE buffer. A low concentration of dissociated ions results in slow hybridization kinetics, exacerbates ionic depletion associated with immobilizing charges (oligonucleotide probes) in the gel, and increases the time required to electrokinetically inject target DNA into the gel. Calculations using 89 mM tris base and 89 mM boric acid, with a pKa of 9.24 for boric acid and a pKa of 8.3 for tris shows a concentration of 1.49 mM each of dissociated tris and dissociated boric acid in 1×TBE buffer.

Example 3.2

Effect of Salt Concentration on DNA Hybridization

In embodiments used to separate nucleic acids, the presence of positive counter ions shields the electrostatic repulsion of negatively charged complementary strands of nucleic acid, resulting in increased rates of hybridization. For example, it is known that increasing the concentration of Na+ ions affects the rate of DNA hybridization in a non-linear manner (see Tsuruoka et al.[15], which is incorporated by reference herein). The hybridization rate increases by about 10 fold when [NaCl] is increased from 10 mM to 1 M of [NaCl], with most of the gain achieved by the time one reaches about 200 mM. At low concentrations of positive counter ions, below about 10 mM, the rate of hybridization is more strongly dependent on salt concentration, roughly proportional to the cube of the salt concentration[6]. Theoretical calculations suggest that the total positive counter ion concentration of 1×TBE is around 5.5 mM (1.5 mM of dissociated tris, and 4 mM of Na+ from the disodium EDTA). At this ion concentration it was possible to achieve focusing however the slow hybridization rates resulted in weak focusing and large final focus spot sizes.

A slow rate of hybridization can lead to weak focusing through an increase in the phase lag between the changes in electric field and changes in mobility. Equation [16] describes the SCODA velocity as being proportional to $\cos(\phi)$, where $\phi$ represents the phase lag between the mobility oscillations and the electric field oscillations. In the case of ssSCODA a phase lag can result from both a slow thermal response as well as from slow hybridization kinetics.

This phase lag results in slower focusing times and larger spot sizes since the final spot size is a balance between the inward SCODA-driven drift, and outward diffusion-driven drift. Faster focusing times are always desirable as this tends to reduce the overall time to enrich a target from a complex mixture. A smaller spot size is also desirable as it improves the ability to discriminate between different molecular species. As discussed above, when performing SCODA focusing under application of a DC bias, the final focus spot will be shifted off center by an amount that depends on both the mobility of the target and the speed of focusing, both of which depend on the strength of the interaction between the target and the gel bound probes. The amount of separation required to discriminate between two similar molecules when focusing under bias therefore depends on the final focus spot diameter. Smaller spot diameters should improve the ability to discriminate between two targets with similar affinity to the gel bound probes.

At the low rates of hybridization achieved with 1×TBE buffer, reliable focusing was only achievable with probe concentrations near 100 μM. Increasing the salt concentration from around 5 mM to 200 mM through the addition of NaCl, while keeping the probe concentration at 100 μM had the effect of reducing the final focus spot size as shown in FIGS. 13A-D. All images in FIGS. 13A-D were taken after a similar amount of focusing time (approximately 5 min), however the increased salinity resulted in increased Joule heating, which required a four fold reduction of field strength to prevent boiling when focusing with 200 mM NaCl. Probe concentrations are 100 μM, 10 μM, 1 μM, and 100 μM, respectively in FIGS. 13A, 13B, 13C and 13D. The buffer used in FIGS. 13A, 13B and 13C was 1×TB with 0.2 M NaCl. The buffer used in FIG. 13D was 1×TBE. Focusing was not reliable at 10 μM and 1 μM probe in 1×TBE and these results are not shown. Under equivalent conditions in this example, addition of 200 mM NaCl to the gel also allowed for focusing of complementary targets at 100 fold lower probe concentrations.

Equation [30] states that the focusing speed is proportional to the electric field strength, so that fact that comparable focusing times are achieved with a four fold reduction in electric field strength suggests that the field normalized focusing speed is considerably faster under high salinity conditions.

Although the total time for focusing was not reduced by the addition of 200 mM NaCl, focusing at lower electric field strength may be desirable in some embodiments because lower field strength can limit the degree of non-specific electrophoretic SCODA that may occur in an affinity matrix in some embodiments. For example, all target nucleic acid molecules will focus irrespective of their sequence in the affinity gels used for sequence specific SCODA in embodiments where the thermal gradient is established by an electric field due to electrophoretic SCODA. The speed of electrophoretic SCODA focusing increases with electric field[13], so decreasing the field strength will have the effect of reducing the non-specific SCODA focusing speed, allowing one to wash non-target DNA molecules from the gel more easily by applying a DC bias.

Example 3.3

Ion Depletion and Bound Charges

The rate at which ions are depleted (or accumulated) at a boundary increases as the fraction of charges that are immobile increases. The 100 μM probe concentration required to achieve efficient concentration in 1×TBE results in 2 mM of bound negative charges within the gel when a 20 nucleotide probe is used, which is comparable to the total amount of dissolved negative ions within the gel (around 5.5 mM). This high proportion of bound charge can result in the formation of regions within the gel that become depleted of ions when a constant electric field is placed across the gel[16-20] as it is during injection and during SCODA focusing under DC bias.

A high salinity running buffer can therefore help to minimize many of the ion depletion problems associated with immobilizing charges in an ssSCODA gel by enabling focusing at lower probe concentrations, as well as reducing the fraction of bound charges by adding additional free charges.

Example 3.4

Denaturation of Double Stranded DNA

Target DNA will not interact with the gel immobilized probes unless it is single stranded. The simplest method for generating single stranded DNA from double stranded DNA is to boil samples prior to injection. One potential problem with this method is that samples can re-anneal prior to injection reducing the yield of the process, as the re-annealed double stranded targets will not interact with the probes and can be washed off of the gel by the bias field. Theoretical calculations show that the rate of renaturation of a sample will be proportional to the concentration of denatured single stranded DNA. Provided target concentration and sample salinity are both kept low, renaturation of the sample can be minimized.

To measure the effect of target concentration on renaturation and overall efficiency, fluorescently labeled double stranded PCR amplicons complementary to gel bound probes were diluted into a 250 μl volume containing about 2 mM NaCl and denatured by boiling for 5 min followed by cooling in an ice bath for 5 min. The sample was then placed in the sample chamber of a gel cassette, injected into a focusing gel and concentrated to the centre of the gel. After concentration was complete the fluorescence of the final focus spot was measured, and compared to the fluorescence of the same quantity of target that was manually pipetted into the centre of an empty gel cassette. This experiment was performed with 100 ng ($2\times10^{11}$ copies) and 10 ng ($2\times10^{10}$ copies) of double stranded PCR amplicons. The 100 ng sample resulted in a yield of 40% and the 10 ng sample resulted in a yield of 80%. This example confirms that lower sample DNA concentration will result in higher yields.

Example 3.5

Phase Lag Induced Rotation

Figure 14:
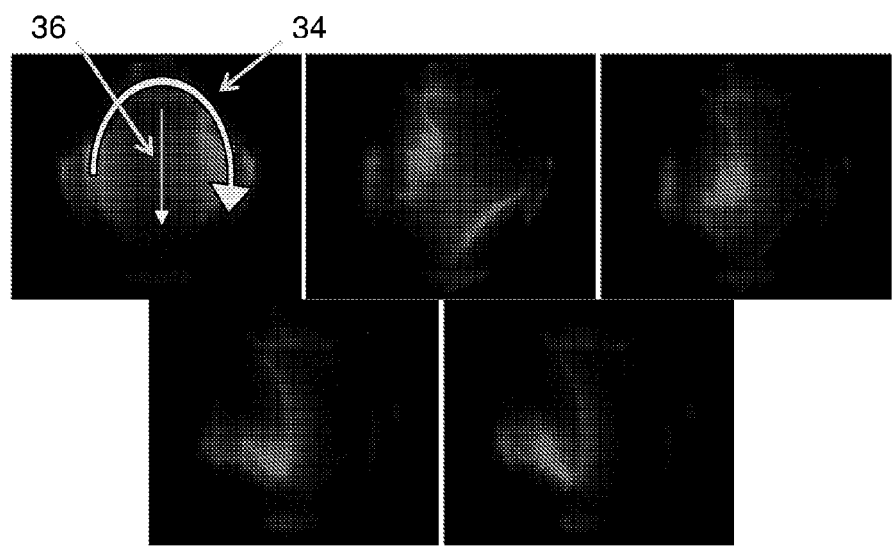
FIG. 14 shows an experiment providing an example of phase lag induced rotations. The field rotation is counter-clockwise, that induces a clockwise rotation of the targets in the gel. Images were taken at 5 minute intervals.

As discussed above, in embodiments in which there is a phase lag between the electric field oscillations and the mobility varying oscillations, a rotational component will be added to the velocity of molecules moving through the affinity matrix. An example of this problem is shown in FIG. 14. The targets shown in FIG. 14 focus weakly under SCODA fields and when a small bias is applied to wash them from the gel, the wash field and the rotational velocity induced by the SCODA fields sum to zero near the bottom left corner of the gel. This results in long wash times, and in extreme cases weak trapping of the contaminant fragments. The direction of rotation of the electric field used to produce SCODA focusing is indicated by arrow 34. The direction of the applied washing force is indicated by arrow 36.

To overcome this problem the direction of the field rotation can be altered periodically. In other examples described herein, the direction of the field rotation was altered every period. This results in much cleaner washing and focusing with minimal dead zones. This scheme was applied during focus and wash demonstrations described above and shown in FIG. 12, an example in which the mismatched target was cleanly washed from the gel without rotation. Under these conditions there is a reduced SCODA focusing velocity due to the phase lag, but there is not an additional rotational component of the SCODA velocity.

Example 3.6

Effect of Secondary Structure

Secondary structure in the target DNA will decrease the rate of hybridization of the target to the immobilized probes. This will have the effect of reducing the focusing speed by increasing the phase lag described in equation [16]. The amount by which secondary structure decreases the hybridization rate depends on the details of the secondary structure. With a simple hairpin for example, both the length of the stem and the loop affect the hybridization rate[9]. For most practical applications of sequence specific SCODA, where one desires to enrich for a target molecule differing by a single base from contaminating background DNA, both target and background will have similar secondary structure. In this case the ability to discriminate between target and background will not be affected, only the overall process time. By increasing the immobilized probe concentration and the electric field rotation period one can compensate for the reduced hybridization rate.

There are potentially cases where secondary structure can have an impact on the ability to discriminate a target molecule from background molecules. It is possible for a single base difference between target and background to affect the secondary structure in such a way that background DNA has reduced secondary structure and increased hybridization rates compared to the target, and is the basis for single stranded conformation polymorphism (SSCP) mutation analysis. This effect has the potential to both reduce or enhance the ability to successfully enrich for target DNA, and care must be taken when designing target and probe sequences to minimize the effects of secondary structure. Once a target molecule has been chosen, the probe position can be moved around the mutation site. The length of the probe molecule can be adjusted. In some cases, oligonucleotides can be hybridized to sequences flanking the region where the probe anneals to further suppress secondary structure.

Example 4.0

Quantitation of Sequence Specific SCODA Performance

The length dependence of the final focus location while focusing under DC bias was measured and shown to be independent of length for fragments ranging from 200 nt to 1000 nt in length; an important result, which implies that ssSCODA is capable of distinguishing nucleic acid targets by sequence alone without the need for ensuring that all targets are of a similar length. Measurements confirmed the ability to enrich for target sequences while rejecting contaminating sequences differing from the target by only a single base, and the ability to enrich for target DNA that differs only by a single methylated cytosine residue with respect to contaminating background DNA molecules.

Example 4.1

Length Independence of Focusing

The ability to purify nucleic acids based on sequence alone, irrespective of fragment length, eliminates the need to ensure that all target fragments are of similar length prior to enrichment. The theory of sequence specific SCODA presented above predicts that sequence specific SCODA enrichment should be independent of target length. However, effects not modeled above may lead to length dependence, and experiments were therefore performed to confirm the length independence of sequence specific SCODA.

According to the theory of thermally driven sequence specific SCODA developed above, the final focus location under bias should not depend on the length of the target strands. Length dependence of the final focus location enters into this expression through the length dependence of the unimpeded mobility of the target $\mu_0$. However, since both $\mu(T_m)$ and a are proportional to $\mu_0$, the length dependence will cancel from this expression. The final focus location of a target concentrated with thermally driven ssSCODA should therefore not depend on the length of the target, even if a bias is present.

There are two potential sources of length dependence in the final focus location, not modeled above, which must also be considered: electrophoretic SCODA in embodiments where the temperature gradient is established by an electric field, and force based dissociation of probe target duplexes. DNA targets of sufficient length (>200 nucleotides) have a field dependent mobility in the polyacrylamide gels used for sequence specific SCODA, and will therefore experience a sequence independent focusing force when focusing fields are applied to the gel. The total focusing force experienced by a target molecule will therefore be the sum of the contributions from electrophoretic SCODA and sequence specific SCODA. Under electrophoretic SCODA, the focusing velocity tends to increase for longer molecules[13], while the DC velocity tends to decrease so that under bias the final focus location depends on length. The second potential source of length dependence in the final focus location is force based dissociation. The theory of affinity SCODA presented above assumed that probe-target dissociation was driven exclusively by thermal excitations. However it is possible to dissociate double stranded DNA with an applied force. Specifically, an external electric field pulling on the charged backbone of the target strand can be used to dissociate the probe-target duplex. The applied electric field will tend to reduce the free energy term $\Delta G$ in equation [22] by an amount equal to the energy gained by the charged molecule moving through the electric field[12]. This force will be proportional to the length of the target DNA as there will be more charges present for the electric field to pull on for longer target molecules, so for a given electric field strength the rate of dissociation should increase with the length of the target.

Figure 15A:
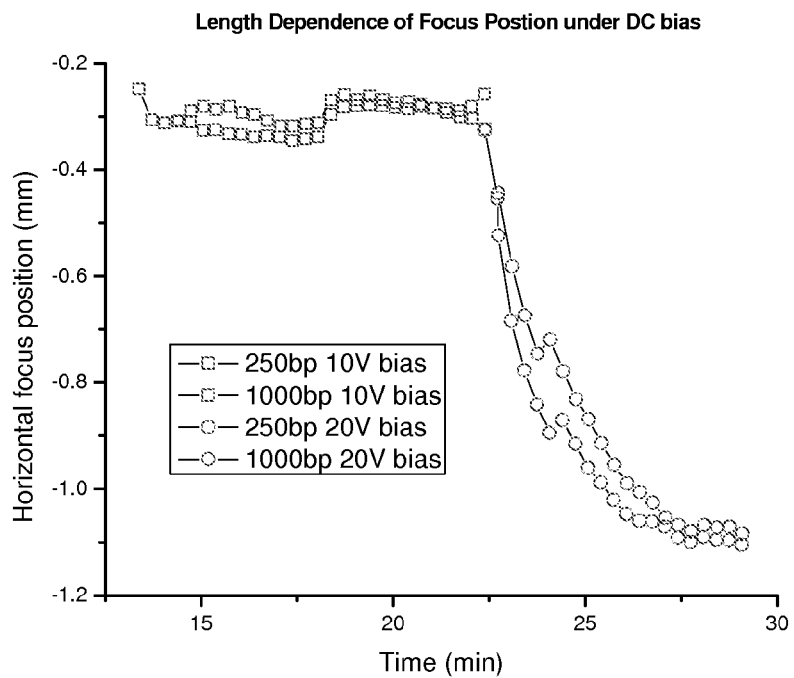
FIG. 15A shows the focus location under bias for 250 bp and 1000 bp fragments labeled with different fluorescent markers, with squares indicating data for the application of a 10 V DC bias and circles indicating data for the application of a 20 V DC bias.
Figure 15B:
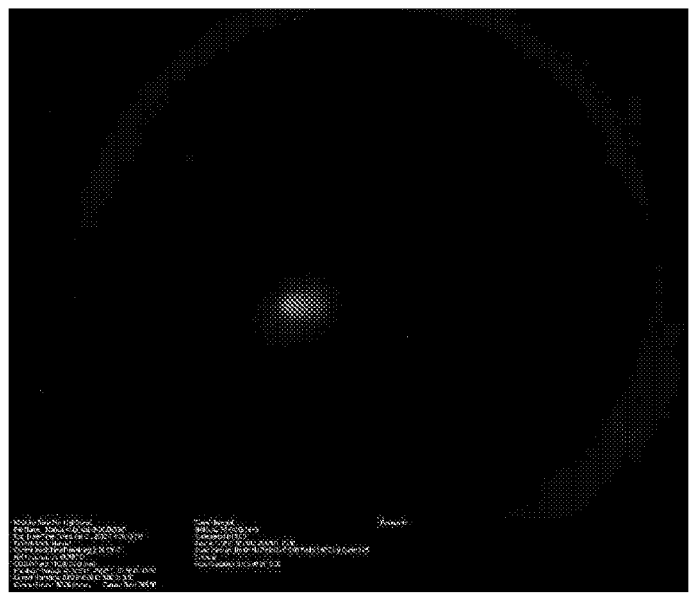
FIG. 15B shows an image of the affinity gel at the end of the run, wherein images showing the location of each fluorescent marker have been superimposed.

To measure whether or not these two effects contribute significantly to the length dependence of the final focus location, two different lengths of target DNA, each containing a sequence complementary to gel immobilized probes, were focused under bias and the final focus location measured and compared. The target DNA was created by PCR amplification of a region of pUC19 that contains a sequence complementary to the probe sequence in Table 3. Two reactions were performed with a common forward primer, and reverse primers were chosen to generate a 250 bp amplicon and a 1000 bp amplicon. The forward primers were fluorescently labeled with 6-FAM and Cy5 for the 250 bp and 1000 bp fragments respectively. The targets were injected into an affinity gel and focused to the centre before applying a bias field. A bias field of 10 V/cm was superimposed over 120 V/cm focusing fields for 10 min at which point the bias was increased to 20 V/cm for an additional 7 min. Images of the gel were taken every 20 sec, with a 1 sec delay between the 6-FAM channel and the Cy5 channel. The field rotation period was 5 sec. Images were post processed to determine the focus location of each fragment. FIGS. 15A and 15B show the focus location versus time for the 250 bp (green) and 1000 bp (red) fragments. FIG. 15B is an image of final focus of the two fragments at the end of the experiment.

There is a small difference in final location that can be attributed to the fact that the two images were not taken at the same phase in the SCODA cycle. This example shows that the final focus position does not depend on length. Thus, under these operating conditions electrophoretic SCODA focusing is much weaker than affinity SCODA focusing, and that affinity SCODA is driven largely by thermal dissociation rather than force-based dissociation. This result confirms that affinity SCODA is capable of distinguishing nucleic acid targets by sequence alone without the need for ensuring that all targets are of a similar length.

Example 4.2

Single Base Mismatch Rejection Ratio

To demonstrate the specificity of ssSCODA with respect to rejection of sequences differing by a single base, different ratios of synthetic 100 nt target DNA containing either a perfect match (PM) or single base mismatch (sbMM) to a gel bound probe, were injected into an affinity gel. SCODA focusing in the presence of DC wash fields was performed to remove the excess sbMM DNA. The PM target sequence was labeled with 6-FAM and the sbMM with Cy5; after washing the sbMM target from the gel the amount of fluorescence at the focus location was quantified for each dye and compared to a calibration run. For the calibration run, equimolar amounts of 6-FAM labeled PM and Cy5 labeled PM target DNA were focused to the centre of the gel and the fluorescence signal at the focus location was quantified on each channel. The ratio of the signal Cy5 channel to the signal on the 6-FAM channel measured during this calibration is therefore the signal ratio when the two dye molecules are present in equimolar concentrations. By comparing the fluorescence ratios after washing excess sbMM from the gel to the calibration run it was possible to determine the amount of sbMM DNA rejected from the gel by washing.

Samples containing target sequences shown in Table 3 were added to the sample chamber and an electric field of 50 V/cm was applied across the sample chamber at 45° C. to inject the sample into a gel containing 10 µM of immobilized probe. Once the sample was injected into the gel, the liquid in the sample chamber was replaced with clean buffer and SCODA focusing was performed with a superimposed DC wash field. A focusing field of 60 V/cm was combined with a DC wash field of 7 V/cm, the latter applied in the direction opposite to the injection field. It was found that this direction for the wash field led to complete rejection of the mismatched target DNA in the shortest amount of time. Table 6 below shows the amount of DNA injected into the gel for each experiment.

TABLE 6

List of targets run for measuring the rejection ratio of affinity SCODA with respect to single base differences.

| Run Description: | Cy5 Labeled Target | 6-FAM Labeled Target |
|---|---|---|
| 1:1 Calibration | 10 fmol PM | 10 fmol PM |
| 100:1 | 1 pmol sbMM | 10 fmol PM |
| 1,000:1 | 10 pmol sbMM | 10 fmol PM |
| 10,000:1 | 100 pmol sbMM | 10 fmol PM |
| 100,000:1 | 1 nmol sbMM | 10 fmol PM |

Figure 16A:
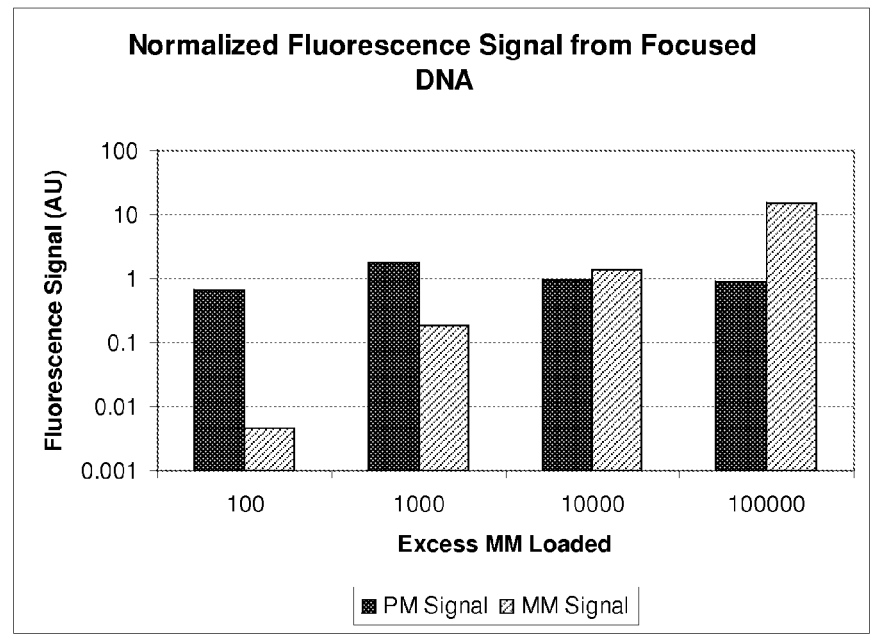
FIGS. 16A and 16B show respectively the normalized fluorescence signal and the calculated rejection ratio of a 100 nucleotide sequence having a single base mismatch as compared with a target DNA molecule according to one example.
Figure 16B:
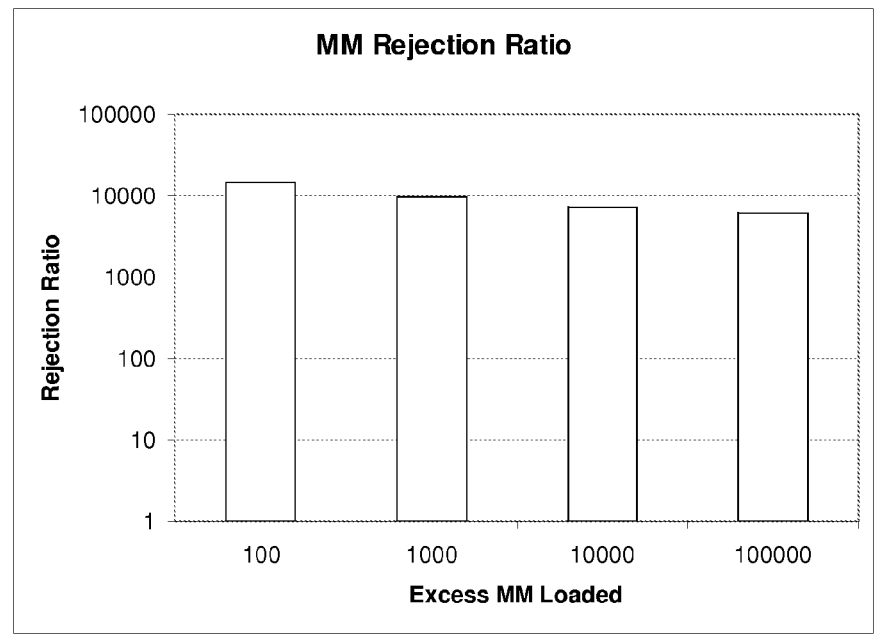

After the mismatched target had been washed from the gel, the focusing fields were turned off and the temperature of the gel was reduced to 25° C. prior to taking an image of the gel for quantification. It was important to ensure that all images used for quantification were taken at the same temperature, since Cy5 fluorescence is highly temperature dependent, with the fluorescence decreasing at higher temperatures. The ratio of fluorescence on the Cy5 and 6-FAM channels were compared to the 1:1 calibration run to determine the rejection ratio for each run. FIGS. 16A and 16B show the results of these experiments. Four different ratios of sbMM:PM were injected into a gel and focused under bias to remove excess sbMM. The PM DNA was tagged with 6-FAM and the sbMM DNA was tagged with Cy5. FIG. 16A shows the fluorescence signal from the final focus spot after excess sbMM DNA had been washed from the gel. The fluorescence signals are normalized to the fluorescence measured on an initial calibration run where a 1:1 ratio of PM-FAM:PMCy5 DNA was injected and focused to the centre of the gel. FIG. 16B shows the rejection ratios calculated by dividing the initial ratio of sbMM:PM by the final ratio after washing.

It was found that rejection ratios of about 10,000 fold are achievable. However it should be noted that images taken during focusing and wash at high sbMM:PM ratios suggest that there were sbMM molecules with two distinct velocity profiles. Most of the mismatch target washed cleanly off of the gel while a small amount was captured at the focus. These final focus spots visible on the Cy5 channel likely consisted of Cy5 labeled targets that were incorrectly synthesized with the single base substitution error that gave them the PM sequence. The 10,000:1 rejection ratio measured here corresponds to estimates of oligonucleotide synthesis error rates with respect to single base substitutions[21], meaning that the mismatch molecule synthesized by IDT likely contains approximately 1 part in 10,000 perfect match molecules. This implies that the residual fluorescence detected on the Cy5 channel, rather than being unresolved mismatch may in fact be Cy5 labeled perfect match that has been enriched from the mismatch sample. Consequently the rejection ratio of ssSCODA may actually be higher than 10,000:1.

Example 4.3

Mutation Enrichment for Clinically Relevant Mutation

The synthetic oligonucleotides used in the example above were purposely designed to maximize the difference in binding energy between the perfect match-probe duplex and the mismatch-probe duplex. The ability of affinity SCODA to enrich for biologically relevant sequences has also been demonstrated. In this example, cDNA was isolated from cell lines that contained either a wild type version of the EZH2 gene or a Y641N mutant, which has previously been shown to be implicated in B-cell non-Hodgkin Lymphoma[22]. 460 bp regions of the EZH2 cDNA that contained the mutation site were PCR amplified using fluorescent primers in order to generate fluorescently tagged target molecules that could be visualized during concentration and washing. The difference in binding energy between the mutant-probe duplex and the wild type-probe duplex at 60° C. was 2.6 kcal/mol compared to 3.8 kcal/mol for the synthetic oligonucleotides used in the previous examples. This corresponds to a melting temperature difference of 5.2° C. for the mutant compared to the wild type. Table 7 shows the free energy of hybridization and melting temperature for the wild type and mutants to the probe sequence.

TABLE 7

Binding energy and melting temperatures of EZH2 targets to the gel bound probe.

| Target | Binding Energy |
|---|---|
| Wild Type | $-161.9 + 0.4646T$ |
|  | $T_m = 57.1°$ C. |
| Y641N Mutant | $-175.2 + 0.4966T$ |
|  | $T_m = 62.3°$ C. |

A 1:1 mixture of the two alleles were mixed together and separated with affinity SCODA. 30 ng of each target amplicon was added to 300 µl of 0.01× sequence specific SCODA running buffer. The target solution was immersed in a boiling water bath for 5 min then placed in an ice bath for 5 min prior to loading onto the gel cassette in order to denature the double stranded targets. The sample was injected with an injection current of 4 mA for 7 min at 55° C. Once injected, a focusing field of 150 V/cm with a 10 V/cm DC bias was applied at 55° C. for 20 min.

Figure 17A:
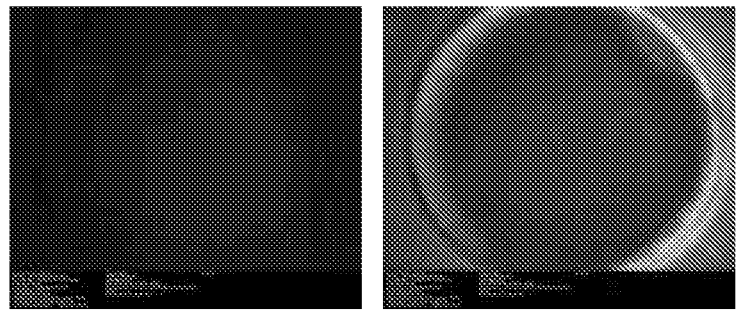
FIGS. 17A, 17B and 17C show enrichment of cDNA obtained from an EZH2 Y641N mutation from a mixture of wild type and mutant amplicons using affinity SCODA with the application of a DC bias. Images were taken at 0 minutes (FIG. 17A), 10 minutes (FIG. 17B), and 20 minutes (FIG. 17C).
Figure 17B:
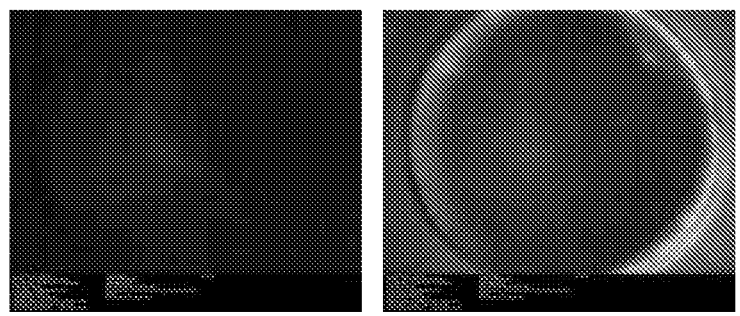
Figure 17C:
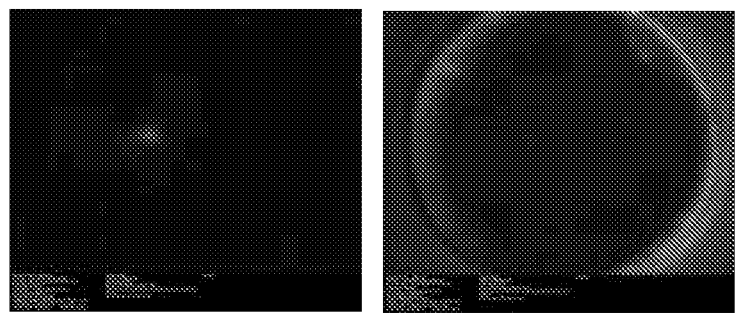

The result of this experiment is shown in FIGS. 17A, 17B and 17C. The behavior of these sequences is qualitatively similar to the higher $T_m$ difference sequences shown in the above examples. The wild type (mismatch) target is completely washed from the gel (images on the right hand side of the figure) while the mutant (perfect match) is driven towards the centre of the gel (images on the left hand side of the figure). In this case the efficiency of focusing was reduced as some of the target re-annealed forming double stranded DNA that did not interact with the gel bound probes.

The lower limit of detection with the optical system used was around 10 ng of singly labeled 460 bp DNA.

Example 5.0

Methylation Enrichment

The ability of affinity SCODA based purification to selectively enrich for molecules with similar binding energies was demonstrated by enriching for methylated DNA in a mixed population of methylated and unmethylated targets with identical sequence.

Figure 18:
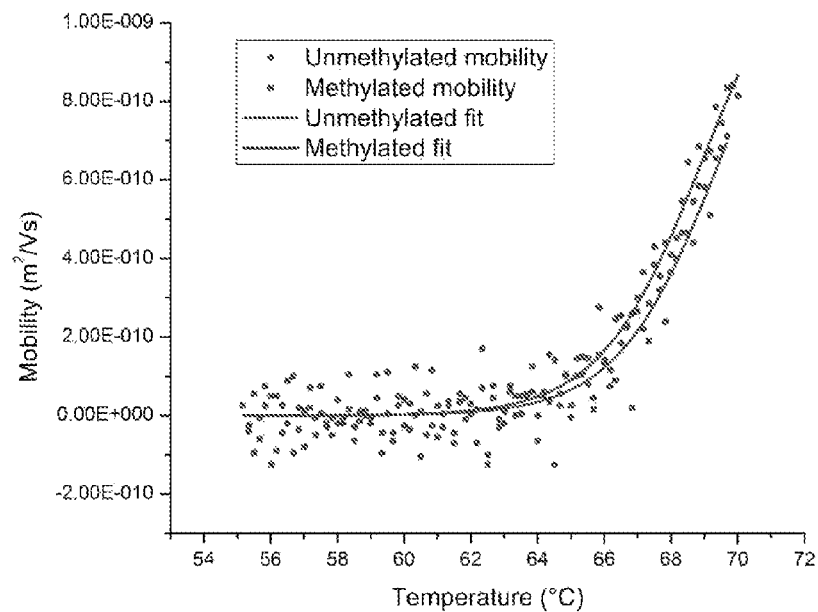
FIG. 18 shows experimental results for the measurement of mobility versus temperature for methylated and unmethylated targets. Data points were fit to equation [23]. Data for the unmethylated target is fit to the curve on the left; data for the methylated target is fit to the curve on the right.

Fluorescently tagged PM oligonucleotides having the sequence set out in Table 3 (SEQ ID NO. 2) were synthesized by IDT with a single methylated cytosine residue within the capture probe region (residue 50 in the PM sequence of Table 3). DC mobility measurements of both the methylated and unmethylated PM strands were performed to generate velocity versus temperature curves as described above; this curve is shown in FIG. 18.

Figure 19:
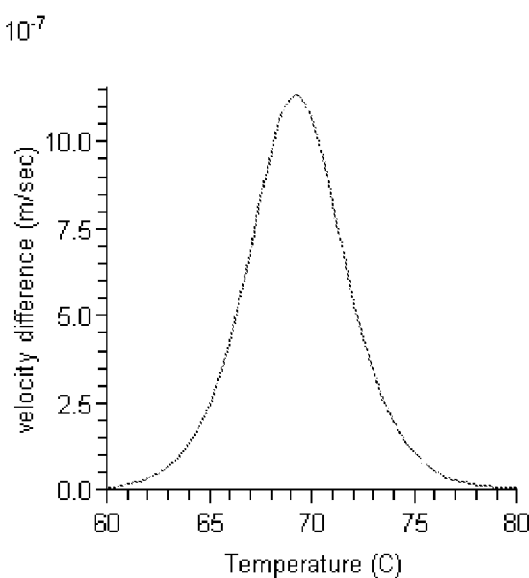
FIG. 19 shows the difference between the two mobility versus temperature curves which were fit to the data from FIG. 18. The maximum value of this difference is at 69.5° C., which is the temperature for maximum separation while performing affinity SCODA focusing with the application of a DC bias.

Fitting of these curves to equation [23] suggests that the difference in binding energy is around 0.19 kcal/mol at 69° C., which is about a third of the thermal energy$^{FN1}$. The curve further suggests that separation of the two targets will be most effective at an operating temperature of around 69° C., where the two fragments have the greatest difference in mobility as shown in FIG. 19. In this example, the maximum value of this difference is at 69.5° C., which is the temperature for maximum separation while performing SCODA focusing under the application of a DC bias.

At 69° C. $k_bT$=0.65 kcal/mol

This temperature is slightly higher than that used in the above examples, and although it should result in better discrimination, focus times are longer as the higher temperature limits the maximum electric field strength one can operate at without boiling the gel.

Figure 20:
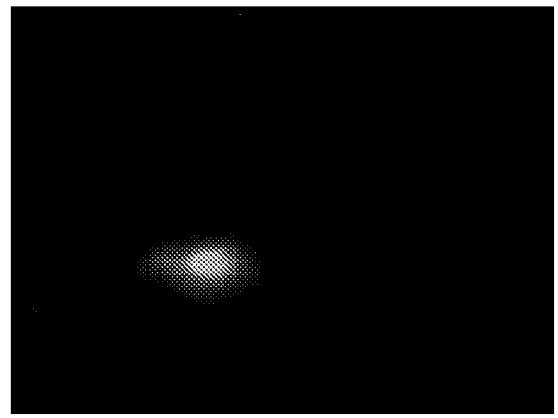
FIG. 20 shows experimental results for the separation of methylated (6-FAM, green) and unmethylated (Cy5, red) targets by using SCODA focusing with an applied DC bias.

Initial focusing tests showed that it is possible to separate the two targets by performing affinity SCODA focusing with a superimposed DC bias. FIG. 20 shows the result of an experiment where equimolar ratios of methylated and unmethylated targets were injected into a gel, focused with a period of 5 sec at a focusing field strength of 75 V/cm and a bias of 14 V/cm at 69° C. Methylated targets were labeled with 6-FAM (green, spot on right) and unmethylated targets were labeled with Cy5 (red, spot on left). The experiment was repeated with the dyes switched, with identical results.

Figure 21A:
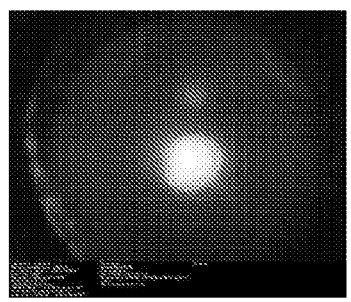
FIGS. 21A-21D show the separation of differentially methylated oligonucloetides using affinity SCODA.
Figure 21B:
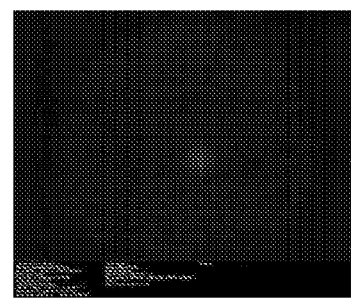
Figure 21C:
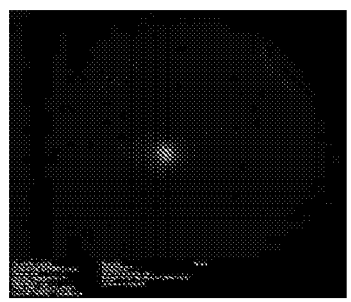
Figure 21D:
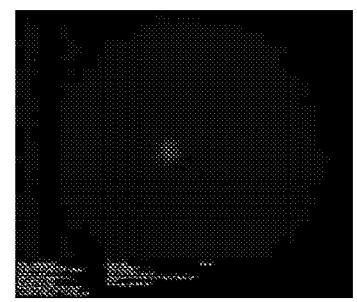

Achieving enrichment by completely washing the unmethylated target from the gel proved to be difficult using the same gel geometry for the above examples, as the gel buffer interface was obscured by the buffer wells preventing the use of visual feedback to control DC bias fields while attempting to wash the unmethylated target from the gel. To overcome this problem gels were cast in two steps: first a gel without probe oligonucleotides was cast in one of the arms of the gel and once the first gel had polymerized the remainder of the gel area was filled with gel containing probe oligonucleotides. The gels were cast such that the interface between the two was visible with the fluorescence imaging system. This system allowed for real time adjustments in the bias voltage so that the unmethylated target would enter the gel without immobilized probes and be quickly washed from the gel, while the methylated target could be retained in the focusing gel. FIGS. 21A-21D show the result of this experiment. FIGS. 21A and 21B show the results of an initial focus before washing unmethylated target from the gel for 10 pmol unmethylated DNA (FIG. 21A) and 0.1 pmol methylated DNA (FIG. 21B). FIGS. 21C and 21D show the results of a second focusing conducted after the unmethylated sequence had been washed from the gel for unmethylated and methylated target, respectively. All images were taken with the same gain and shutter settings.

In this experiment a 100 fold excess of unmethylated target was injected into the gel, focused to the centre without any wash fields applied. The targets were then focused with a bias field to remove the unmethylated target, and finally focused to the centre of the gel again for fluorescence quantification. Fluorescence quantification of these images indicates that the enrichment factor was 102 fold with losses of the methylated target during washing of 20%. This experiment was repeated with the dye molecules swapped (methylated Cy5 and unmethylated 6-FAM) with similar results.

Example 6.0

Multiplexed Affinity SCODA

Two different oligonucleotide probes described above, one having affinity for EZH2 and one having affinity for pUC, were cast in a gel at a concentration of 10 μM each to provide an affinity matrix containing two different immobilized probes. A 100 nucleotide target sequence with affinity for the EZH2 probe and a theoretical melting temperature of 62.3° C. was labeled with Cy5. A 100 nucleotide target sequence with affinity for the pUC probe and a theoretical melting temperature of 70.1° C. was labeled with FAM. The theoretical difference in melting temperature between the two target molecules is 7.8° C.

Figure 22A:
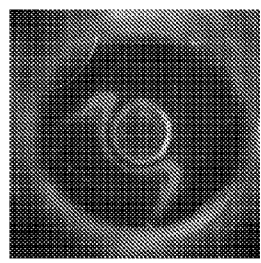
FIGS. 22A-22K show the results of the differential separation of two different sequences in the same affinity matrix using different oligonucleotide probes.
Figure 22B:
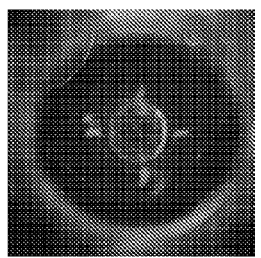
Figure 22C:
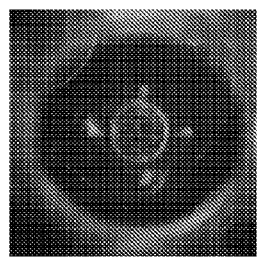
Figure 22D:
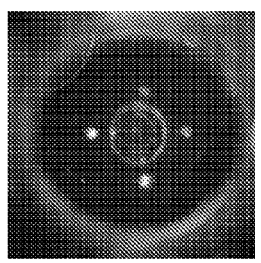
Figure 22E:
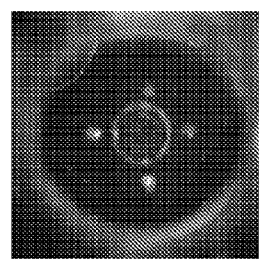

The target molecules were loaded on the affinity gel (FIG. 22A), and focusing was conducted with the temperature beneath the gel boat maintained at 55° C. (FIGS. 22B, focusing after two minutes, and 22C, after four minutes). The EZH2 target focused under these conditions (four red spots), while the pUC target focused only weakly under these conditions (three diffuse green spots visible on the gel). The central extraction well did not contain buffer during the initial portions of this experiment, resulting in the production of four focus spots, rather than a single central focus spot. The temperature beneath the gel was then increased to 62° C., a temperature increase of 7° C. (FIGS. 22D, focusing two minutes after temperature increase, and 22E, after four minutes), resulting in the formation of four clear focus spots for the pUC target. The EZH2 target remained focused in four tight spots at this higher temperature.

Figure 22F:
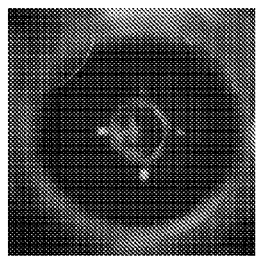
Figure 22G:
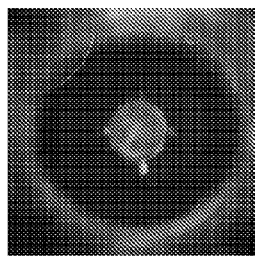
Figure 22H:
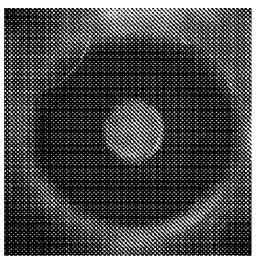

The temperature beneath the gel was reduced to 55° C. and buffer was added to the central extraction well. Application of SCODA focusing fields at this temperature resulted in the EZH2 target being selectively concentrated into the central extraction well (diffuse red spot visible at the centre of FIGS. 22F, 0.5 minutes, and 22G, 1 minute) while the pUC target remained largely focused in four spots outside the central extraction well. The temperature beneath the gel was increased to 62° C., a temperature increase of 7° C. Within two minutes, the pUC target had been focused into the central extraction well (FIG. 22H, diffuse red and green fluorescence visible at the centre of the gel).

Figure 22I:
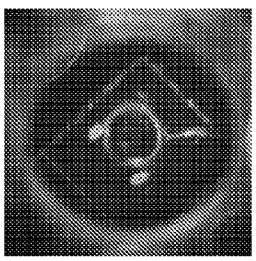
Figure 22J:
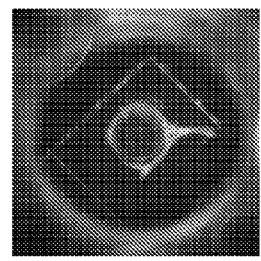
Figure 22K:
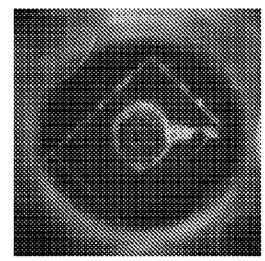

A second experiment was conducted under similar conditions as the first. After focusing the EZH2 target at 55° C. and the pUC target at 62° C. as described above, a DC washing bias was applied to the gel with the temperature beneath the gel maintained at 55° C. Under these conditions, the EZH2 target experienced a greater bias velocity than the pUC target. The focus spot for the EZH2 target shifted more quickly after the application of the bias field (red spot moving to the right of the gel in FIGS. 22I, 6 minutes after application of bias field, 22J, after 12 minutes, and 22K, after 18 minutes). The focus spot for the EZH2 target was also shifted a farther distance to the right within the gel. In contrast, the focus spot for the pUC target shifted more slowly (initial green focus spots still largely visible in FIG. 22I after 6 minutes, shifting to the right through FIG. 22J, 12 minutes, and 22K, 18 minutes), and was not shifted as far to the right as the focus spot for the EZH2 target by the washing bias.

Affinity SCODA Yield vs Purity

Because affinity SCODA relies on repeated interactions between target and probe to generate a non-dispersive velocity field for target molecules, while generating a dispersive field for contaminants (so long as a washing bias is applied), high specificity can be achieved without sacrificing yield. If one assumes that the final focus spot is Gaussian, which is justified by calculating the spot size for a radial velocity field balanced against diffusion[13], then the spot will extend all the way out to the edge of the gel. Here diffusion can drive targets off the gel where there is no restoring focusing force and an applied DC bias will sweep targets away from the gel where they will be lost. In this manner the losses for ssSCODA can scale with the amount of time one applies a wash field; however the images used to generate FIGS. 13A-13D indicate that in that example the focus spot has a full width half maximum (FWHM) of 300 μm and under bias it sits at approximately 1.0 mm from the gel centre. If it is assumed that there is 10 fmol of target in the focus spot, then the concentration at the edge of the gel where a bias is applied is 1e-352 M; there are essentially zero target molecules present at the edges of the gel where they can be lost under DC bias. This implies that the rate at which losses accumulate due to an applied bias (i.e. washing step) is essentially zero. Although the desired target may be lost from the system in other ways, for example by adsorbing to the sample well prior to injection, running off the edge of the gel during injection, re-annealing before or during focusing (in the case of double stranded target molecules), or during extraction, all of these losses are decoupled from the purity of the purified target.

Aspects of the exemplary embodiments and examples described above may be combined in various combinations and subcombinations to yield further embodiments of the invention. To the extent that aspects of the exemplary embodiments and examples described above are not mutually exclusive, it is intended that all such combinations and subcombinations are within the scope of the present invention. It will be apparent to those of skill in the art that embodiments of the present invention include a number of aspects. Accordingly, the scope of the claims should not be limited by the preferred embodiments set forth in the description and examples, but should be given the broadest interpretation consistent with the description as a whole.

REFERENCES

1. Marziali A, Pel J, Bizzotto D, Whitehead L A. Novel electrophoresis mechanism based on synchronous alternating drag perturbation. Electrophoresis 2005; 26(1):82-90.
2. Bird A P. CpG-Rich Islands and the Function of DNA Methylation. Nature 1986; 321(6067):209-213.
3. Freier S M, Altmann K H. The ups and downs of nucleic acid duplex stability: structure-stability studies on chemically-modified DNA:RNA duplexes. Nucleic Acids Research 1997; 25(22):4429-4443.
4. Sanghvi Y S, Hoke G D, Freier S M, Zounes M C, Gonzalez C, Cummins L, Sasmor H, Cook P D. Antisense Oligodeoxynucleotides—Synthesis, Biophysical and Biological Evaluation of Oligodeoxynucleotides Containing Modified Pyrimidines. Nucleic Acids Research 1993; 21(14):3197-3203.
5. Warmlander S, Sponer J E, Sponer J, Leijon M. The influence of the thymine C5 methyl group on spontaneous base pair breathing in DNA. Journal of Biological Chemistry 2002; 277(32):28491-28497.
6. Wetmur J G. Hybridization and Renaturation Kinetics of Nucleic-Acids Annual Review of Biophysics and Bioengineering 1976; 5:337-361.
7. Wetmur J G, Davidson N. Kinetics of Renaturation of DNA. Journal of Molecular Biology 1968; 31(3):349-&.
8. Meinkoth J, Wahl G. Hybridization of Nucleic-Acids Immobilized on Solid Supports. Analytical Biochemistry 1984; 138(2):267-284.
9. Tsourkas A, Behlke M A, Rose S D, Bao G. Hybridization kinetics and thermodynamics of molecular beacons. Nucleic Acids Research 2003; 31(4):1319-1330.

10. Craig M E, Crothers D M, Doty P. Relaxation Kinetics of Dimer Formation by Self Complementary Oligonucleotides. Journal of Molecular Biology 1971; 62(2):383.
11. Nakane J, Wiggin M, Marziali A. A nanosensor for transmembrane capture and identification of single nucleic acid molecules. Biophysical Journal 2004; 87(1): 615-621.
12. Nakane J J. Detection and analysis of nucleic acids using nanometer-scale pores. Vancouver: University of British Columbia; 2006.
13. Pel J. A novel electrophoretic mechanism and separation parameter for selective nucleic acid concentration based on synchronous coefficient of drag alteration (SCODA). Vancouver: University of British Columbia; 2009.
14. Zuker M. Mfold web server for nucleic acid folding and hybridization prediction. Nucleic Acids Research 2003; 31(13):3406-3415.
15. Tsuruoka M, Yano K, Ikebukuro K, Nakayama H, Masuda Y, Karube I. Optimization of the rate of DNA hybridization and rapid detection of methicillin resistant Staphylococcus aureus DNA using fluorescence polarization. Journal of Biotechnology 1996; 48(3):201-208.
16. Spencer M. Anomalous Conductivity Zones in Electrophoresis 0.1. Basic Theory for 2-Ion Systems. Electrophoresis 1983; 4(1):36-41.
17. Spencer M. Anomalous Conductivity Zones in Electrophoresis 0.2. Theory for 3-Ion Systems and for Changes in pH. Electrophoresis 1983; 4(1):41-45.
18. Spencer M, Kirk J M. Anomalous Conductivity Zones in Electrophoresis 0.3. Experimental Tests of the Theory. Electrophoresis 1983; 4(1):46-52.
19. Figeys D, Renborg A, Dovichi N J. Spatial and Temporal Depletion of Ions from Noncrosslinked Denaturing Polyacrylamide in Capillary Electrophoresis. Electrophoresis 1994; 15(12): 1512-1517.
20. Coope R J N, Marziali A. Contaminant-induced current decline in capillary array electrophoresis. Electrophoresis 2005; 26(11):2128-2137.
21. Tian J D, Gong H, Sheng N J, Zhou X C, Gulari E, Gao X L, Church G. Accurate multiplex gene synthesis from programmable DNA microchips. Nature 2004; 432 (7020): 1050-1054.
22. Morin R D, Johnson N A, Severson T M, Mungall A J, An J H, Goya R, Paul J E, Boyle M, Woolcock B W, Kuchenbauer F and others. Somatic mutations altering EZH2 (Tyr641) in follicular and diffuse large B-cell lymphomas of germinal-center origin. Nature Genetics 2010; 42(2):181-U124.

---

What is claimed is:

1. A method of separating differentially methylated nucleic acid molecules, comprising:
   providing first and second nucleic acid molecules, the first and second nucleic acids molecules being at least 95% identical in sequence but being differentially methylated,
   contacting a matrix comprising an oligonucleotide probe with the first and second nucleic acids, wherein the difference between the binding energy of the first nucleic acid molecule to the oligonucleotide probe and the binding energy of the second nucleic acid molecule to the oligonucleotide probe is less than about 4 kcal/mol; and
   applying a time-varying electric field to the matrix while synchronously varying the mobility of the first and second nucleic acids, thereby separating the first and second nucleic acid molecules.

2. The method of claim 1, further comprising collecting the first nucleic acid molecule from the matrix.

3. The method of claim 1, further comprising collecting the second nucleic acid molecule from the matrix.

4. The method of claim 1, wherein the time-varying electric field varies the mobility of the first and second nucleic acids.

5. The method of claim 4, wherein the time-varying electric field varies the mobility by causing Joule heating within the matrix.

6. A method of separating differentially methylated nucleic acid molecules, comprising:
   providing first and second nucleic acid molecules, the first and second nucleic acids molecules being at least 95% identical in sequence but being differentially methylated,
   contacting a matrix comprising an oligonucleotide probe with the first and second nucleic acids, wherein the difference between the melting temperature of the first nucleic acid molecule complexed with the oligonucleotide probe and the melting temperature of the second nucleic acid molecule complexed with the oligonucleotide probe is less than about 10° C.; and
   applying a time-varying electric field to the matrix while synchronously varying the mobility of the first and second nucleic acids, thereby separating the first and second nucleic acid molecules.

7. The method of claim 6, wherein the difference in temperatures is less than about 3° C.

8. The method of claim 1, wherein the first and second nucleic acid molecules are between 100 and 1000 nucleotides in length.

9. The method of claim 1, wherein the first and second nucleic acid molecules are less than 100 nucleotides in length.

10. A method of separating differentially methylated nucleic acid molecules, comprising:
    providing first and second nucleic acid molecules, the first nucleic acid molecule and the second nucleic acid molecule are methylated at different nucleotides;
    contacting a matrix comprising an oligonucleotide probe with the first and second nucleic acids; and
    applying a time-varying electric field to the matrix while synchronously varying the mobility of the first and second nucleic acids, thereby separating the first and second nucleic acid molecules.

11. The method of claim 1, wherein the oligonucleotide probe is complimentary to at least a portion of the first and second nucleic acid molecules.

12. The method of claim 1, wherein the first nucleic acid molecule originates from a fetus, the second nucleic acid molecule originates from a mother of the fetus and both the first and second nucleic acids are obtained from a blood sample from the mother.

13. The method of claim 1, wherein both the first and the second nucleic acids comprise a gene implicated in cancer.

14. The method of claim 1, further comprising amplifying or sequencing the first or the second nucleic acid.

15. A method of separating differentially methylated nucleic acid molecules, comprising:
    providing first and second nucleic acid molecules, the first and second nucleic acids molecules being at least 95% identical in sequence but being differentially methylated;
    contacting a matrix comprising a plurality of different oligonucleotide probes with the first and second nucleic acids; and
    applying a time-varying electric field to the matrix while synchronously varying the mobility of the first and second nucleic acids, thereby separating the first and second nucleic acid molecules.

16. The method of claim 15, wherein a first portion of the plurality of different oligonucleotide probes is complimentary to the first nucleic acid molecule and a second portion of the plurality of different oligonucleotide probes is complementary to a third nucleic acid molecule, and wherein the method additionally comprises separating the third nucleic acid molecule from a fourth nucleic acid molecule.

17. The method of claim 16, further comprising separating the first nucleic acid molecule from the third nucleic acid molecule.

18. The method of claim 1, wherein the first and second nucleic acids molecules are at least 98% identical in sequence.

* * * * *

UNITED STATES PATENT AND TRADEMARK OFFICE
CERTIFICATE OF CORRECTION

PATENT NO. : 9,434,938 B2  Page 1 of 1
APPLICATION NO. : 13/968907
DATED : September 6, 2016
INVENTOR(S) : Marziali et al.

It is certified that error appears in the above-identified patent and that said Letters Patent is hereby corrected as shown below:

In the Specification

Column 1, Line 13 please insert a "Statement of Government Rights" section after the "Reference to Related Application" section and before the "Field of the Invention" section as follows:

--Statement of Government Rights
This invention was made with government support under R01 HG004873 awarded by the National Institutes of Health. The Government has certain rights in the invention.--

Signed and Sealed this
Twenty-eighth Day of February, 2017

Michelle K. Lee
*Director of the United States Patent and Trademark Office*

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct

<400> SEQUENCE: 1
actggccgtc gttttact                                                   18

<210> SEQ ID NO 2
<211> LENGTH: 100
<212> TYPE: DNA
<213> ORGANISM: Artificial Sequence
<220> FEATURE:
<223> OTHER INFORMATION: Synthetic Construct

<400> SEQUENCE: 2
cgattaagtt gagtaacgcc actattttca cagtcataac catgtaaaac gacggccagt      60
gaattagcga tgcatacctt gggatcctct agaatgtacc                          100

<210> SEQ ID NO 3
<211> LENGTH: 100
<212> TYPE: DNA
<213> ORGANISM: Artificial Sequence
<220> FEATURE:
<223> OTHER INFORMATION: Synthetic Construct

<400> SEQUENCE: 3
cgattaagtt gagtaacgcc actattttca cagtcataac catgtaaaac tacggccagt      60
gaattagcga tgcatacctt gggatcctct agaatgtacc                          100
```